US011234967B2

(12) United States Patent
Parkin et al.

(10) Patent No.: US 11,234,967 B2
(45) Date of Patent: Feb. 1, 2022

(54) USE OF 3-[5-AMINO-4-(3-CYANOBENZOYL)-PYRAZOL-1-YL]-N-CYCLOPROPYL-4-METHYLBENZAMIDE IN THE PREVENTION OR REDUCTION OF ACUTE EXACERBATIONS OF CHRONIC OBSTRUCTIVE PULMONARY DISEASE

(71) Applicant: MEREO BIOPHARMA 1 LIMITED, London (GB)

(72) Inventors: Jacqueline Parkin, London (GB); Alastair McKinnon, London (GB)

(73) Assignee: MEREO BIOPHARMA 1 LIMITED, London (GB)

( * ) Notice: Subject to any disclaimer, the term of this patent is extended or adjusted under 35 U.S.C. 154(b) by 0 days.

(21) Appl. No.: 15/733,213

(22) PCT Filed: Dec. 11, 2018

(86) PCT No.: PCT/GB2018/053591
§ 371 (c)(1),
(2) Date: Jun. 10, 2020

(87) PCT Pub. No.: WO2019/116022
PCT Pub. Date: Jun. 20, 2019

(65) Prior Publication Data
US 2020/0383950 A1 Dec. 10, 2020

(30) Foreign Application Priority Data

Dec. 11, 2017 (GB) .................................... 1720622
Dec. 11, 2017 (GB) .................................... 1720624
Feb. 13, 2018 (GB) .................................... 1802353
Feb. 13, 2018 (GB) .................................... 1802354

(51) Int. Cl.
*A61K 31/415* (2006.01)
(52) U.S. Cl.
CPC .................................. *A61K 31/415* (2013.01)
(58) Field of Classification Search
CPC combination set(s) only.
See application file for complete search history.

(56) References Cited

U.S. PATENT DOCUMENTS

| 6,899,099 | B2 | 5/2005 | Andersson et al. |
| 9,339,491 | B2 | 5/2016 | Ford |
| 10,603,306 | B2 | 3/2020 | Orford et al. |

FOREIGN PATENT DOCUMENTS

| WO | 2005/009973 A1 | 2/2005 |
| WO | 2005/110452 A2 | 11/2005 |
| WO | 2007/096151 A2 | 8/2007 |
| WO | 2013/139809 A1 | 9/2013 |
| WO | 2017/153702 A1 | 9/2017 |

OTHER PUBLICATIONS

International Search Report and Written Opinion dated Mar. 6, 2019 in PCT/GB2018/053591 (18 pages).
Compton et al., "The Novartis View on Emerging Drugs and Novel Targets for the Treatment of Chronic Obstructive Pulmonary Disease", Pulm Pharmacol Ther. Oct. 2013;26(5):562-73. doi: 10.1016/j.pupt.2013.05.009. Epub Jun. 4, 2013.
Perera et al., "Inflammatory Changes, Recovery and Recurrence at COPD Exacerbation", Eur Respir J. Mar. 2007;29(3):527-34. doi: 10.1183/09031936.00092506. Epub Nov. 15, 2006.
Marks-Konczalik et al., "A Post-Hoc Subgroup Analysis of Data From a Six Month Clinical Trial Comparing the Efficacy and Safety of Losmapimod in Moderate-Severe COPD Patients With ≤2% and >2% Blood Eosinophils", Respir Med. Jul. 2015; 109(7):860-9. doi: 10.1016/j.rmed.2015.05.003. Epub May 20, 2015.
Wedzicha et al., "Effectiveness of Acumapimod Oral P38 Inhibitor in the Treatment of Acute Severe Exacerbations of COPD: Results of the AETHER Phase II Trial", 814 Late Breaking Clinical Trials and First Reports in Asthma and COPD / Mini Symposium/ Monday, May 21 /9:15 AM-11:15 AM/ Room 33 A-C (Upper Level)—San Diego Convention Center.
De Buck et al., "Population PK-PD Model for Tolerance Evaluation to the p38 MAP Kinase Inhibitor BCT197", CPT Pharmacometrics Syst Pharmacol. Dec. 2015;4(12):691-700 doi: 10.1002/psp4.12037. Epub Nov. 9, 2015.
European Patent Office Communication pursuant to Article 94(3) EPC, dated Dec. 13, 2019 in EP 18819365.0 (4 pages).
International Search Report and Written Opinion dated Mar. 6, 2019 in PCT/GB2018/053590 (16 pages).
Pascoe et al., "Biological Effects of p38 MAPK Inhibitor Losmapimod Does Not Translate to Clinical Benefits in COPD", Respir Med. Sep. 2017; 130:20-26. doi: 10.1016/j.rmed.2017.07.002. Epub Jul. 4, 2017.
D. Hammaker and G. S. Firestein, ""Go upstream, young man": lessons learned from the p38 saga" Ann Rheum Dis. Jan. 2010; 69 (Suppl 1): i77-i82 doi:10.1136/ard.2009 119479 (14 pages).
International Preliminary Report on Patentability issued in PCT/GB2016/050636 dated Sep. 11, 2018 (8 pages).
International Search Report and Written Opinion issued in PCT/GB2016/050635 dated Mar. 3, 2017 (15 pages).
Trial record for NCT01332097, Safety & Efficacy of BCT197A2201 in Chronic Obstructive Pulmonary Disease (COPD) Patients Presenting with an Exacerbation, last update posted Feb. 20, 2014, US National Library of Medicine, retrieved from https://ClinicalTrials.gov on Dec. 19, 2019 (6 pages).
Ikeda et al., "Pharmacological treatment in acute exacerbations of chronic obstructive pulmonary disease", Drugs Aging Feb. 1998;12(2):129-37. Review.

(Continued)

*Primary Examiner* — Kamal A Saeed
(74) *Attorney, Agent, or Firm* — Wolff IP a Prof Corp; Jessica Wolff

(57) ABSTRACT

The invention relates to dosage regimens for administering pharmaceutical compositions comprising 3-[5-amino-4-(3-cyanobenzoyl)-pyrazol-1-yl]-N-cyclopropyl-4-methylbenzamide for the treatment of a human patient suffering from COPD, or suffering from an acute exacerbation of COPD, or at risk of developing an acute exacerbation of COPD, or to prevent a reoccurrence of an acute exacerbation of COPD, or to prevent a treatment failure of an acute exacerbation of COPD, and to methods of prevention or reduction in the rate of acute exacerbations of COPD in a human patient.

20 Claims, 10 Drawing Sheets

(56) References Cited

OTHER PUBLICATIONS

Norman et al., "Investigational p38 inhibitors for the treatment of chronic obstructive pulmonary disease", Expert Opin Investig Drugs. Mar. 2015;24(3):383-92. doi: 10.1517/13543784.2015.1006358. Epub Jan. 20, 2015. Review.
International Search Report and Written Opinion issued in PCT/GB2016/050636 dated Mar. 3, 2017 (12 pages).
Barbera et al., "Pulmonary hypertension in chronic obstructive pulmonary disease", Eur. Respir. J., 2003, 21:892-905.
Office Action dated 04/20/20217 in U.S. Appl. No. 15/143,356 (105 pages).
Office Action dated Jun. 26, 2019 in U.S. Serial No. 16/082,772 (29 pages).
Office Action dated Apr. 3, 2019 in U.S. Appl. No. 16/082,765 (11 pages).
International Preliminary Report on Patentability issued in PCT/GB2016/050635 dated Sep. 11, 2018 ( 8 pages).
Barnes et al., "Systemic manifestations and comorbidities of COPD", Eur Respir J 2009; 33: 1165-1185, DOI: 10.1183/09031936.00128008.
Bourdin et al., "Recent advances in COPD: pathophysiology, respiratory physiology and clinical aspects, including comorbidities", Eur Respir Rev 2009; 18:114, 198-212, DOI: 10.1183/09059180.00005509.
Halper-Stromberg et al., "Systemic Markers of Adaptive and Innate Immunity Are Associated with Chronic Obstructive Pulmonary Disease Severity and Spirometric Disease Progression", Am J Respir Cell Mol Biol vol. 58, Iss 4, pp. 500-509, Apr. 2018.
U.S. Appl. No. 16/793,922, filed Feb. 18, 2020 (1075 pages).
European Patent Office Communication pursuant to Article 94(3) EPC, dated Nov. 28, 2018 in EP 18819366.8 (7 pages).
European Patent Office Communication pursuant to Article 94(3) EPC, dated Apr. 3, 2020 in EP 18819366.8 (11 pages).
European Patent Office Communication pursuant to Article 94(3) EPC, dated Jul. 17, 2020 in EP 18819366.8 (4 pages).
Acetals; http://goldbook.iupac.org/ A00062. html; accessed Jan. 15, 2016.
Acid; IUPAC Goldbook; http://goldbook.iupac.org/A00071.html; accessed Jan. 15, 2016.
Celli and Vestbo in Am. J. Respir. Grit. Care Med. vol. 183, 2011, pp. 287-291.
Chopra et al.; Therapeutic potential of inhaled p38 mitogen-activated protein kinase inhibitors for inflammatory pulmonary diseases; 2008; Expert Opinion on Investigational Drugs; 17(1 ): 1411-1425.
Derivative; Merriam Webster; http://www.merriam-webster.com/dictionary/derivative; accessec Jan. 15, 2016.
Elssner et al.; "Isolation, Identification, and Synthesis of y-Butyrobetainyl-CoA and Crotonobetainyl-CoA, Compounds nvolved in Carnitine metabolism of *E. coli*"; 2000; Biochemistry; 39:10761-10769.
Esters; IUPAC Goldbook; http://goldbook.iupac.org/E02219.html; accessed Jan. 15, 2015.
Han et al. (1995) Biochim. Biophys. Acta 1265(2-3):224-7.
Hemiacetals; http://goldbook.iupac.org/H02774.html; accessed Jan. 15, 2016.
Hemiketals; http://goldbook.iupac.org/H02776.html; accessed Jan. 15, 2016.
Aaron et al., "Outpatient Oral Prednisone after Emergency Treatment of Chronic Obstructive Pulmonary Disease", New England Journal of Medicine, 2003, 348:2618-25.
Jiang et al. (1996) J. Biol. Chem. 271 (30):17920-6.
Jones et al in Chest vol. 139, No. 6, 2011, pp. 1388-1394.
Ketals; http://goldbook.iupac.org/K03376. htm l; accessed Jan. 15, 2016.
Leidy et al in Am. J. Respir. Grit. Care Med. vol. 183, 2011, pp. 323-329.
Leidy et al in International Society for Pharmacoeconomics and Outcomes Research, vol. 13,No. 8,2010,pp. 965-975.
Lomas et al.; "An Oral Inhibitor of p38 MAP Kinase Reduces Plasma Fibrinogen in Patients With Chronic Obstructive Pulmonary Disease"; J Clin Pharmacol.; Mar. 2012; 52(3): 416-24. doi: 10.1177/0091270010397050. Epub Nov. 16, 2011.
Prodrug; http://dictionary.reference.com/browse/prodrug; accessed Jan. 15, 2016.
Haifeng et al., "Effect of sequential treatment with syndrome differentiation on acute exacerbation of chronic obstructive pulmonary disease and AECOPD Risk-Window; study protocol for a randomized placebo-controlled trial", Trials, Biomed Central, London, GB, Apr. 20, 2012, vol. 13, No. 1, p. 40.
Chung, "p38 Mitogen-Activated Protein Kinase Pathways in Asthma and COPD", Chest, 2011, 139(6):1470-1479.

USE OF 3-[5-AMINO-4-(3-CYANOBENZOYL)-PYRAZOL-1-YL]-N-CYCLOPROPYL-4-METHYLBENZAMIDE IN THE PREVENTION OR REDUCTION OF ACUTE EXACERBATIONS OF CHRONIC OBSTRUCTIVE PULMONARY DISEASE

CROSS-REFERENCE TO RELATED APPLICATIONS

The present invention is filed under 35 U.S.C. § 371 as the U.S. national phase of International Patent Application No. PCT/GB2018/053591, filed Dec. 11, 2018, which designated the United States, and which claims the benefit of priority to GB Patent Application No. 1720622.8 filed Dec. 11, 2017, and to GB Patent Application No. 1720624.4 filed Dec. 11, 2017, and to GB Patent Application No. 1802354.9 filed Feb. 13, 2018, and to GB Patent Application No. 1802353.1 filed Feb. 13, 2018. each of which is hereby incorporated by reference in its entirety including all tables, figures, and claims.

FIELD OF THE INVENTION

This invention relates to organic compounds and their use as pharmaceuticals, more specifically, to a novel use of 3-[5-amino-4-(3-cyanobenzoyl)-pyrazol-1-yl]-N-cyclopropyl-4-methylbenzamide or a pharmaceutically acceptable derivative thereof, namely in the prevention or reduction of acute exacerbations of chronic obstructive pulmonary disease.

BACKGROUND OF THE INVENTION

A large number of cytokines participate in the inflammatory response, including interleukin-1 (IL-1), IL6, IL-8 and TNF-α. Overproduction of cytokines such as IL-1 and TNF-α are implicated in a wide variety of diseases, including acute exacerbations of chronic obstructive pulmonary disease (AECOPD).

Evidence in human patients indicates that protein antagonists of cytokines are effective in treating chronic inflammatory diseases. International patent application WO2005/009973 discloses various pyrazole- and imidazole-based compounds or pharmaceutically acceptable derivatives thereof that have cytokine inhibitory activity. It discloses such compounds can be used to treat conditions associated with p38 kinases, especially p38α and β kinases, including chronic obstructive pulmonary disease (COPD). WO2005/009973 discloses 3-[5-amino-4-(3-cyanobenzoyl)-pyrazol-1-yl]-N-cyclopropyl-4-methylbenzamide as one such novel pyrazole-based p38 kinase inhibitor and describes processes for its preparation. 3-[5-Amino-4-(3-cyanobenzoyl)-pyrazol-1-yl]-N-cyclopropyl-4-methylbenzamide has the following chemical structure:

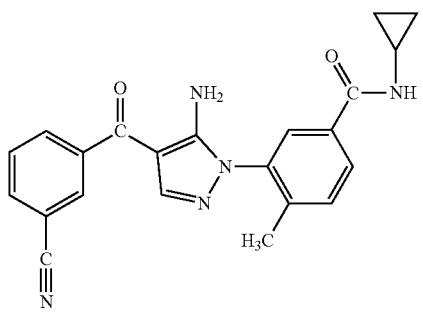 [SMILES: Cc1ccc(C(=O)NC2CC2)cc1-n1ncc(C(=O)c2cccc(C#N)c2)c1N]

This compound is also known as BCT197.

Chronic obstructive pulmonary disease (COPD) and acute exacerbations of chronic obstructive pulmonary disease (AECOPD) are distinct indications or at least concern distinct disease states that require different treatment. Acute exacerbations of COPD are associated with increased mortality, accelerated decline in lung function, and impaired quality of life.

WO 2013/139809 discloses the use of 3-[5-amino-4-(3-cyanobenzoyl)-pyrazol-1-yl]-N-cyclopropyl-4-methylbenzamide and pharmaceutically acceptable derivatives thereof and use of these compounds in treating AECOPD. A single oral dose of 3-[5-Amino-4-(3-cyanobenzoyl)-pyrazol-1-yl]-N-cyclopropyl-4-methylbenzamide was administered and the effect on recovery of AECOPD to the stable disease state was studied. A single dose administered orally accelerates the recovery to the stable disease state.

It has surprisingly been found that the dosage regimens of the present invention are particularly effective for preventing or reducing the rate of recurrent acute exacerbations of COPD.

SUMMARY OF THE INVENTION

In a first aspect, the present invention provides a pharmaceutical composition for the treatment of a human patient suffering from COPD, comprising administering to the patient an effective dose or doses of 3-[5-amino-4-(3-cyanobenzoyl)-pyrazol-1-yl]-N-cyclopropyl-4-methylbenzamide over a period of not longer than seven days with at least one day between every dose, and repeating the administration to the patient of the effective dose or doses of 3-[5-amino-4-(3-cyanobenzoyl)-pyrazol-1-yl]-N-cyclopropyl-4-methylbenzamide or a pharmaceutically acceptable derivative thereof after a 3-[5-amino-4-(3-cyanobenzoyl)-pyrazol-1-yl]-N-cyclopropyl-4-methylbenzamide treatment hiatus of at least 1 month from the start of the preceding administration.

Hereafter, reference to 3-[5-amino-4-(3-cyanobenzoyl)-pyrazol-1-yl]-N-cyclopropyl-4-methylbenzamide will include reference to the compound per se and pharmaceutically acceptable derivatives thereof.

In a second aspect, the present invention provides a pharmaceutical composition for the treatment of a human patient suffering from COPD, comprising administering to the patient three doses of 3-[5-amino-4-(3-cyanobenzoyl)-pyrazol-1-yl]-N-cyclopropyl-4-methylbenzamide over a period of not longer than seven days with at least one day between every dose, and repeating the administration to the patient of the three doses of 3-[5-amino-4-(3-cyanobenzoyl)-pyrazol-1-yl]-N-cyclopropyl-4-methylbenzamide thereof after a 3-[5-amino-4-(3-cyanobenzoyl)-pyrazol-1-yl]-N-cyclopropyl-4-methylbenzamide treatment hiatus of at least 1 month from the start of the preceding administration.

In a third aspect, the invention provides a method for the prevention or reduction in the rate of acute exacerbations of COPD in a human patient, comprising administering to the human patient three separate therapeutically effective doses of 3-[5-amino-4-(3-cyanobenzoyl)-pyrazol-1-yl]-N-cyclopropyl-4-methylbenzamide over a period of not longer than seven days with at least one day between every dose, and repeating the administration to the patient of the three doses of 3-[5-amino-4-(3-cyanobenzoyl)-pyrazol-1-yl]-N-cyclopropyl-4-methylbenzamide after a 3-[5-amino-4-(3-cyanobenzoyl)-pyrazol-1-yl]-N-cyclopropyl-4-methylbenzamide treatment hiatus of at least 1 month from the start of the preceding administration.

In a fourth aspect, the invention provides a method for the prevention or reduction in the rate of acute exacerbations of COPD in a human patient, comprising: (a) administering to the human patient three separate therapeutically effective doses of 3-[5-amino-4-(3-cyanobenzoyl)-pyrazol-1-yl]-N-cyclopropyl-4-methylbenzamide over a period of not longer than seven days with at least one day between every dose; (b) discontinuing the administration to the patient with 3-[5-amino-4-(3-cyanobenzoyl)-pyrazol-1-yl]-N-cyclopropyl-4-methylbenzamide for a period of at least 1 month (measured from the start of the preceding administration); and (c) administering to the human patient three separate therapeutically effective doses of 3-[5-amino-4-(3-cyanobenzoyl)-pyrazol-1-yl]-N-cyclopropyl-4-methylbenzamide over a period of not longer than seven days with at least one day between every dose.

In a fifth aspect, the present invention provides a pharmaceutical composition for the treatment of a human patient suffering from an acute exacerbation of COPD or at risk of developing an acute exacerbation of COPD, comprising administering to the patient an effective dose or doses of 3-[5-amino-4-(3-cyanobenzoyl)-pyrazol-1-yl]-N-cyclopropyl-4-methylbenzamide over a period of not longer than seven days with at least one day between every dose, and repeating the administration to the patient of the effective dose or doses of 3-[5-amino-4-(3-cyanobenzoyl)-pyrazol-1-yl]-N-cyclopropyl-4-methyl benzamide or a pharmaceutically acceptable derivative thereof after a 3-[5-amino-4-(3-cyanobenzoyl)-pyrazol-1-yl]-N-cyclopropyl-4-methylbenzamide treatment hiatus of at least 1 month from the start of the preceding administration.

In a sixth aspect, the present invention provides a pharmaceutical composition for the prevention of a reoccurrence of an acute exacerbation of COPD in a human patient suffering from an acute exacerbation of COPD, comprising administering to the patient three doses of 3-[5-amino-4-(3-cyanobenzoyl)-pyrazol-1-yl]-N-cyclopropyl-4-methylbenzamide over a period of not longer than seven days with at least one day between every dose. The human patient may not suffer from a reoccurrence of an acute exacerbation of COPD for at least 30 days after the last dose of 3-[5-amino-4-(3-cyanobenzoyl)-pyrazol-1-yl]-N-cyclopropyl-4-methylbenzamide in the administration, or at least 60 days, or at least 90 days, or at least 120 days, or at least 150 days, or at least 180 days. The administration to the patient of the three doses of 3-[5-amino-4-(3-cyanobenzoyl)-pyrazol-1-yl]-N-cyclopropyl-4-methylbenzamide may be repeated after a 3-[5-amino-4-(3-cyanobenzoyl)-pyrazol-1-yl]-N-cyclopropyl-4-methylbenzamide treatment hiatus of at least 1 month from the start of the preceding administration.

In a seventh aspect, the present invention provides a pharmaceutical composition for the prevention of a treatment failure of an acute exacerbation of COPD in a human patient suffering from an acute exacerbation of COPD, comprising administering to the patient three doses of 3-[5-amino-4-(3-cyanobenzoyl)-pyrazol-1-yl]-N-cyclopropyl-4-methylbenzamide over a period of not longer than seven days with at least one day between every dose. The human patient may not suffer from a treatment failure within 1 day after the last dose of 3-[5-amino-4-(3-cyanobenzoyl)-pyrazol-1-yl]-N-cyclopropyl-4-methylbenzamide in the administration, preferably within 2 days, more preferably within 5 days, more preferably within 7 days, most preferably within 14 days after the last dose of 3-[5-amino-4-(3-cyanobenzoyl)-pyrazol-1-yl]-N-cyclopropyl-4-methylbenzamide in the administration. The administration to the patient of the three doses of 3-[5-amino-4-(3-cyanobenzoyl)-pyrazol-1-yl]-N-cyclopropyl-4-methylbenzamide may be repeated after a 3-[5-amino-4-(3-cyanobenzoyl)-pyrazol-1-yl]-N-cyclopropyl-4-methylbenzamide treatment hiatus of at least 1 month from the start of the preceding administration.

The invention also provides a kit comprising at least one, or at least three, therapeutically effective dose of 3-[5-amino-4-(3-cyanobenzoyl)-pyrazol-1-yl]-N-cyclopropyl-4-methylbenzamide or a pharmaceutically acceptable derivative thereof, and instructions for treating a human patient in accordance with any of the above numbered aspects of the invention, said instructions comprising directions for administering the at least one dose, or at least three, in accordance with any of the above numbered aspects of the invention.

Essentially, the treatment of the present invention is a prophylactic treatment of AECOPD. It amounts to a low frequency maintenance therapy for preventing or reducing AECOPD. The administration of the composition of 3-[5-amino-4-(3-cyanobenzoyl)-pyrazol-1-yl]-N-cyclopropyl-4-methylbenzamide for the first time (i.e., the single or course of multiple doses that are administered over the initial period of not longer than seven days) will be known as the first administration. This is essentially a period of administration whereafter treatment ceases (the "hiatus") and there is no treatment with 3-[5-amino-4-(3-cyanobenzoyl)-pyrazol-1-yl]-N-cyclopropyl-4-methylbenzamide until a further period of administration takes place after the at least one month. The repeat period of administration of 3-[5-amino-4-(3-cyanobenzoyl)-pyrazol-1-yl]-N-cyclopropyl-4-methylbenzamide that takes place at least 1 month after the start of the first administration will be known as the second administration. Any additional administration of 3-[5-amino-4-(3-cyanobenzoyl)-pyrazol-1-yl]-N-cyclopropyl-4-methylbenzamide that takes place after the second administration will be known as further or numbered administrations (e.g., the third, fourth, fifth administration, etc.).

Within a period of administration, i.e., in the first administration, the patient will take one or more doses. These will be referred to a single dose or a course of doses (where a plurality of doses is taken).

Thus, in a preferred embodiment, within each period of administration, i.e., the first, second or third, a course of three separate doses are taken for the period of not longer than seven days.

In a further preferred embodiment, within each period of administration, i.e., the first, second or third, a course of three separate doses are taken for the period of not longer than five days.

With regard to any preceding aspect of the invention, the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide is preferably at least 2 months, preferably about 3 months from the start of the preceding administration. The treatment hiatus can also be longer, for example, at least 4, 5 or 6 months after the start of the preceding administration. Most preferably, the repeat administration (i.e., second, third, fourth, etc., administration) is taken about 3 months (+ or −1 week) after the start of the preceding administration.

The 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide is preferably less than 7 months, more preferably less than 6 months, more preferably less than 5 months, more preferably less than 4 months after the start of the preceding administration.

Preferably the composition or method according to any aspect above comprises administering three separate doses of a pharmaceutical composition comprising 3-[5-amino-4-(3-cyanobenzoyl)-pyrazol-1-yl]-N-cyclopropyl-4-methylbenzamide, wherein the dosing is on days 1, 4 and 7. In a highly preferred embodiment of the invention, the composition or method according to any aspect above comprises administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, over a period of five days with at least one day between every dose administration.

In a most preferred embodiment, the composition or method according to any aspect above comprises administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, wherein the dosing is on days 1, 3 and 5.

In the above embodiments, the three separate doses constitute the administration relating to the first, second, third or further administration as defined above. Thus, each "administration" of the three doses of 3-[5-amino-4-(3-cyanobenzoyl)-pyrazol-1-yl]-N-cyclopropyl-4-methylbenzamide is then punctuated by the treatment hiatus when defined. Then a further "administration" of three doses may take place, followed by a further treatment hiatus, and so forth. Such sequential administrations followed by the treatment hiatus preferably results in the effective reduction or elimination of further acute exacerbations of COPD.

Preferably the composition or method according to any aspect above comprises administering the second administration of 3-[5-amino-4-(3-cyanobenzoyl)-pyrazol-1-yl]-N-cyclopropyl-4-methylbenzamide three months after the start of the first administration of 3-[5-amino-4-(3-cyanobenzoyl)-pyrazol-1-yl]-N-cyclopropyl-4-methylbenzamide or a pharmaceutically acceptable derivative thereof.

Further repeat administrations may take place after the first and second administrations of 3-[5-amino-4-(3-cyanobenzoyl)-pyrazol-1-yl]-N-cyclopropyl-4-methylbenzamide or a pharmaceutically acceptable derivative thereof. For example, the repeat administrations of 3-[5-amino-4-(3-cyanobenzoyl)-pyrazol-1-yl]-N-cyclopropyl-4-methylbenzamide may be chronic. Therefore, the patient may take first, second, third, fourth, . . . n administrations, where n is an integer of 5 to 150.

The Global Initiative for Chronic Obstructive Lung Disease (GOLD) has classified the severity of airflow limitation in COPD based on post-bronchodilator $FEV_1$ into four categories: GOLD 1-GOLD 4. Pocket guide to COPD diagnosis, management and prevention, A guide for health care professionals, Global Initiative for Chronic Obstructive Lung Disease, Inc, 2016. The composition, methods and kits of the present invention are intended to be particularly useful in the treatment of COPD 3 and COPD 4, and also in COPD 2 patients who are about to extend into COPD 3 or COPD 4, i.e., used to prevent GOLD 3 and 4 stage disease. It is known that with each exacerbation, patients are less likely to reach baseline levels of respiratory function. This leads to a vicious cycle wherein the more severe the acute exacerbations a patient has, the longer the exacerbations will take to remit, and the less likely to return to the pre-exacerbation health, leading to increasing susceptibility to more frequent acute exacerbations, getting worse each time, decreasing quality of life. This can be fatal. It is in these specific patients, the optional additional fourth dose may be given in addition to the previous three doses, but within the same 7 day period.

The invention also provides a kit comprising at least six separate therapeutically effective doses of 3-[5-amino-4-(3-cyanobenzoyl)-pyrazol-1-yl]-N-cyclopropyl-4-methylbenzamide or a pharmaceutically acceptable derivative thereof, and instructions for treating a human patient suffering from COPD, said instructions comprising directions for administering the first, second and third doses separately over a period of not longer than seven days with at least one day between every dose administration, and directions for administering the fourth, fifth and sixth doses separately over a period of not longer than seven days with at least one day between every dose administration, said fourth dose being administered at least 1 month after the administration of the first dose.

The invention also provides a kit comprising three separate therapeutically effective doses of 3-[5-amino-4-(3-cyanobenzoyl)-pyrazol-1-yl]-N-cyclopropyl-4-methylbenzamide, and instructions for treating a human patient suffering from AECOPD, said patient having <2% blood eosinophils, said instructions comprising directions for administering said doses separately over a period of not longer than seven days with at least one day between every dose administration. In a preferred embodiment the dosing is on days 1, 3 and 5.

In a preferred embodiment, there is provided a pharmaceutical composition for the treatment of a human patient suffering from COPD, comprising administering to the patient three doses of 3-[5-amino-4-(3-cyanobenzoyl)-pyrazol-1-yl]-N-cyclopropyl-4-methylbenzamide over a period of not longer than seven days with at least one day between every dose; stopping administration of 3-[5-amino-4-(3-cyanobenzoyl)-pyrazol-1-yl]-N-cyclopropyl-4-methylbenzamide for a period of about 3 months (+ or −1 week), and administering to the patient a further three doses of 3-[5-amino-4-(3-cyanobenzoyl)-pyrazol-1-yl]-N-cyclopropyl-4-methylbenzamide over a period of not longer than seven days with at least one day between every dose.

In a further preferred embodiment, there is provided a method for the prevention or reduction in the rate of acute exacerbations of COPD in a human patient, comprising administering to the patient three doses of 3-[5-amino-4-(3-cyanobenzoyl)-pyrazol-1-yl]-N-cyclopropyl-4-methylbenzamide over a period of not longer than seven days with at least one day between every dose; stopping administration of 3-[5-amino-4-(3-cyanobenzoyl)-pyrazol-1-yl]-N-cyclopropyl-4-methylbenzamide for a period of about 7 to 13 weeks, more preferably 10 to 12 weeks, and administering to the patient a further three doses of 3-[5-amino-4-(3-cyanobenzoyl)-pyrazol-1-yl]-N-cyclopropyl-4-methylbenzamide over a period of not longer than seven days with at least one day between every dose.

DETAILED DESCRIPTION OF THE INVENTION

Figure 1:
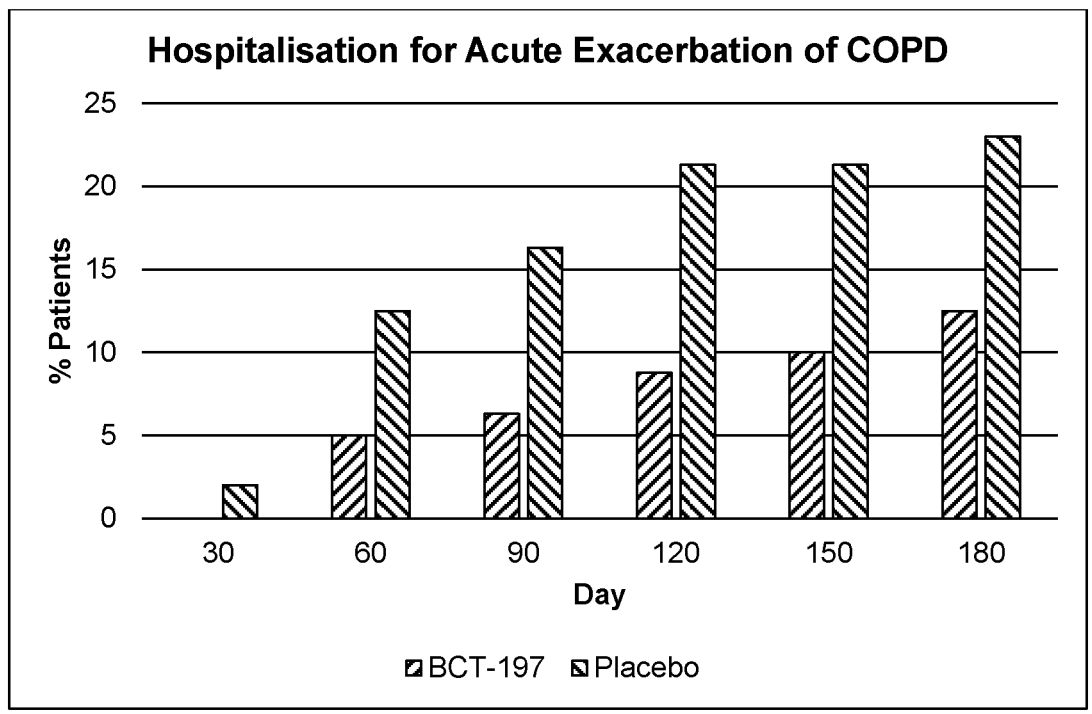
FIG. 1: Occurrence of new acute exacerbations of COPD that required hospitalisation.

The present invention concerns a novel use of 3-[5-amino-4-(3-cyanobenzoyl)-pyrazol-1-yl]-N-cyclopropyl-4-methylbenzamide or a pharmaceutically acceptable derivative thereof, namely in the prevention or reduction in exacerbations of chronic obstructive pulmonary disease.

3-[5-Amino-4-(3-cyanobenzoyl)-pyrazol-1-yl]-N-cyclopropyl-4-methylbenzamide is herein known as BCT197.

Chronic obstructive pulmonary disease (COPD) and acute exacerbations of chronic obstructive pulmonary disease (AECOPD) are distinct indications or at least concern distinct disease states that require different treatment.

COPD is a common preventable and treatable disease that is characterised by persistent airflow limitation that is usually progressive and associated with an enhanced chronic inflammatory response in the airways and the lung to noxious particles of gases. COPD affects more than 80 million people worldwide. It is currently the fourth most frequent cause of death in the world and has been predicted to become the third most frequent cause of death by 2030. Characteristic symptoms of the disease include dyspnea, chronic cough and chronic sputum production. Of these dyspnoea is usually the most prominent and distressing symptom. The main pathophysiological features of COPD are expiratory airflow limitation and air trapping, which manifest as lung hyperinflation and dynamic lung hyperinflation during increased ventilation. This lung hyperinflation contributes to the dyspnoea and resultant activity limitations during stable disease. As the disease progresses, the severity of dyspnoea and other symptoms increases and quality of life for the patient decreases.

Treatment of COPD in its stable chronic disease state typically involves the patient self-administering a long-acting bronchodilator, for example a long-acting β2-agonist (LABA) or a long-acting muscarinic antagonist (LAMA) alone or in combination with a corticosteroid (ICS). These compounds are generally formulated for pulmonary administration up to four times a day using one or more inhalation devices. Such treatment is intended to provide a maintenance therapy, relieving symptoms and helping to prevent acute exacerbations.

Patients who have COPD, especially moderate or severe COPD, may experience an acute exacerbation i.e. a sudden and serious worsening of their condition that requires hospitalisation to return the patient to a stable condition. Physicians typically treat patients experiencing an acute exacerbation with oral steroids (for example prednisone) and/or antibiotics and/or oxygen, but the clinical benefit, especially for oral steroids, is marginal. On average a patient will need to spend 8.4 days in hospital to recover to the previous stable disease state, although this varies from country to country due to differences in clinical practice and hospitalisation costs. Sometimes the recovery is not complete. Some acute exacerbations prove fatal.

According to the present invention, preferably there are administrable doses, preferably unit doses, to be administered over a period of 7 days, and there must be at least one day between each dose administration. Preferably, the dose administration takes place every other day. Preferably, each separate dose has at least a 36 hour period between each administration, preferably at least 42 hours between each administration. Preferred administration schedules of the first administration include Day 1, Day 3, Day 5; Day 1, Day 3, Day 6; Day 1, Day 3, Day 7; Day 1, Day 4, Day 6; Day 1, Day 4, Day 7; or Day 1, Day 5, Day 7. Most preferably, administration schedules include Day 1, Day 3, Day 5 or Day 1, Day 3, Day 6. Most preferably dosing is on days 1, 3 and 5.

Preferred administration schedules of the second administration include Day 1, Day 3, Day 5; Day 1, Day 3, Day 6; Day 1, Day 3, Day 7; Day 1, Day 4, Day 6; Day 1, Day 4, Day 7; or Day 1, Day 5, Day 7 relative to when the first dose is taken within this three dose administration grouping. Most preferably, administration schedules include Day 1, Day 3, Day 5 or Day 1, Day 3, Day 6. Most preferably dosing is on days 1, 3 and 5.

Analogous dosing schedules apply to the second and subsequent administrations of each three dose grouping (in the event that such subsequent administrations take place at all).

FIGS. 1 to 4 of WO 2017/153702 show the dose profiles for 3-[5-amino-4-(3-cyanobenzoyl)-pyrazol-1-yl]-N-cyclopropyl-4-methylbenzamide given on days 1, 4 and 7 respectively.

In a highly preferred embodiment, any of the methods, compositions or kits disclosed above comprise administering three doses separately over a period of five to seven days, with at least one day between every dose administration. Preferably the dosing is on days 1, 3 and 5.

Each of the three doses is for parenteral, oral or pulmonary delivery. Preferably oral dosage forms include oral liquids, suspensions, elixirs or solid dosage forms such as tablets capsules and sublingual tablets. Preferably, each of the oral doses is in the same physical form, i.e., solid oral dosage form, liquid oral dosage form, injection or DPI. Injection, or parenteral dosing, includes sub-cutaneous, intramuscular and intravenous injection. It will be understood to the skilled person that in the case of serious acute exacerbations, the patient may be unable to accept solid oral dosage forms such as tablets, capsules, sublingual tablets and the like, and so the first administration may be given by oral solution, oral suspension, or parenteral administration, and subsequent administrations may be given either by the same delivery vehicle or given by alternative delivery vehicle such as tablet or capsules or sublingual tablets once the patient is able to accept these dosage forms. Preferably, each of the doses of the three dose administration regimen is suitable for oral or parenteral delivery. More preferably, each of the doses of the three dose administration regimen is suitable for oral delivery. Even more preferably, each of the doses is an oral solid dosage form. Most preferably, each of the doses is a capsule or a tablet.

The term liquid oral dosage form is intended to mean administration in the form of a solution or a suspension formulation. Pulmonary delivery is usually via inhalation of a powder or solution. The skilled person understands the processes and excipients that can be used for providing pulmonary delivery. The drug substance may be micronized.

Preferably, the treatment is discontinued after the three doses have been administered to the patient over the 7 (preferably 5) day period. Preferably, there is a gap of at least 3 weeks before a second or further dosage regimen of the present invention is administered, preferably, at least about 3 months (+ or −1 week). In some embodiments there is a gap of at least 2 weeks before a second or further dosage regimen of the present invention is administered, preferably, at least 4 weeks, preferably at least 3 months, most preferably not until a further exacerbation of the COPD is encountered.

The compositions, methods and kits according to the present invention have been found to be particularly effective in preventing or reducing the acute exacerbations of COPD. In an embodiment, alleviating a symptom comprises reducing the frequency of exacerbations. The dosage regime according to the present invention has been found to be particularly effective at extending the time between acute exacerbations in AECOPD. The inventors have shown that treatment according to the present invention achieves baseline levels of inflammatory markers more quickly and then increases the length of time until the next exacerbation of COPD, leading to better health of the patient.

In a particularly preferred embodiment according to any of the numbered aspects of the invention, the amount of the dose of 3-[5-amino-4-(3-cyanobenzoyl)-pyrazol-1-yl]-N-cyclopropyl-4-methylbenzamide is reduced over the course of the three separate administrations. This may be referred to as a descending dosage regimen. Thus, in a preferred embodiment, the initial dose of 3-[5-amino-4-(3-cyanobenzoyl)-pyrazol-1-yl]-N-cyclopropyl-4-methylbenzamide is at least 20% greater than either of the subsequent doses, preferably at least 30% greater, more preferably 40% greater, most preferably between 50% and 100% greater than the subsequent doses. The third dose may be a smaller dose than the second dose. Preferably, the second and third doses are about the same weight. Thus, preferably the ratio of the first dose to either the second and/or third dose of 3-[5-amino-4-(3-cyanobenzoyl)-pyrazol-1-yl]-N-cyclopropyl-4-methylbenzamide is in the range of 1:0.8-1:0.2, preferably 1:0.6-1:0.4.

The therapeutically effective oral dose of 3-[5-amino-4-(3-cyanobenzoyl)-pyrazol-1-yl]-N-cyclopropyl-4-methylbenzamide or a pharmaceutically acceptable derivative thereof, when given orally, is preferably in the range of 10 mg-75 mg, preferably 20 mg-75 mg, preferably 35 mg-75 mg, for example about 25, 30, 35, 40, 50, 60, 70 or 75 mg.

According to the first aspect of the invention, the therapeutically effective oral unit dose of 3-[5-amino-4-(3-cyanobenzoyl)-pyrazol-1-yl]-N-cyclopropyl-4-methylbenzamide or a pharmaceutically acceptable derivative thereof, when given orally, is preferably in the range of 10 mg-75 mg, preferably 20 mg-75 mg, preferably 35 mg-75 mg, for example about 25, 30, 35, 40, 50, 60, 70 or 75 mg, most preferably between 40 mg and 75 mg inclusive.

In the descending dosage regimen referred to above, preferably the first oral dose of 3-[5-amino-4-(3-cyanobenzoyl)-pyrazol-1-yl]-N-cyclopropyl-4-methylbenzamide is in the range of 10 mg-75 mg, preferably 20 mg-80 mg, preferably 35 mg-75 mg. Most preferably the first oral dose is 75 mg.

Preferably, each of the doses is in the same physical form. Preferably, each of the doses is administered via the same route.

In the descending dosage regimen referred to above, preferably the second oral dose of 3-[5-amino-4-(3-cyanobenzoyl)-pyrazol-1-yl]-N-cyclopropyl-4-methylbenzamide is in the range of 5 mg-60 mg, preferably 10 mg-50 mg, preferably 20 mg-40 mg. Most preferably the second oral dose is 40 mg.

In the descending dosage regimen referred to above, preferably the third oral dose of 3-[5-amino-4-(3-cyanobenzoyl)-pyrazol-1-yl]-N-cyclopropyl-4-methylbenzamide is in the range of 5 mg-60 mg, preferably 10 mg-50 mg, preferably 20 mg-40 mg. Most preferably the third oral dose is 40 mg.

In the descending dosage regimen referred to above, preferably, the first oral dose of 3-[5-amino-4-(3-cyanobenzoyl)-pyrazol-1-yl]-N-cyclopropyl-4-methylbenzamide is in the range of 40 mg-75 mg, the second dose of 3-[5-amino-4-(3-cyanobenzoyl)-pyrazol-1-yl]-N-cyclopropyl-4-methylbenzamide is in the range of 20 mg-40 mg, and the third dose of 3-[5-amino-4-(3-cyanobenzoyl)-pyrazol-1-yl]-N-cyclopropyl-4-methylbenzamide is in the range of 20 mg-40 mg, with the proviso that the first dose is greater than either the second or third dose. More preferably, the first oral dose is 50 mg-75 mg, followed by second and third doses at 30-60 mg, most preferably the second and third doses are about 40 mg. Most preferably the second and third doses are the same dose.

In one embodiment, the first oral dose of 3-[5-amino-4-(3-cyanobenzoyl)-pyrazol-1-yl]-N-cyclopropyl-4-methylbenzamide is about 75 mg, the second oral dose of 3-[5-amino-4-(3-cyanobenzoyl)-pyrazol-1-yl]-N-cyclopropyl-4-methylbenzamide is about 40 mg, and the third oral dose of 3-[5-amino-4-(3-cyanobenzoyl)-pyrazol-1-yl]-N-cyclopropyl-4-methylbenzamide is about 40 mg.

The dosage regimen, particularly the descending dosage regimen according to any of the numbered aspects of the present invention, provides a pharmacokinetic (pk) profile for 3-[5-amino-4-(3-cyanobenzoyl)-pyrazol-1-yl]-N-cyclopropyl-4-methylbenzamide where the dose achieves a mean $C_{max}$ of about 1.0 to about 9.0 µM, preferably of about 2.0 to about 6.0 µM. Further, >99% enzyme inhibition is preferably achieved for greater than 3 days following administration of the first dose, preferably greater than 5 days following the first dose.

If administered parenterally, the therapeutically effective dose of 3-[5-amino-4-(3-cyanobenzoyl)-pyrazol-1-yl]-N-cyclopropyl-4-methylbenzamide or a pharmaceutically acceptable derivative thereof, is preferably in the range of 15 mg-60 mg, preferably 18 mg-50 mg, for example about 18, 20, 25, 30, 35, 40. In the descending dosage regimen referred to above, preferably the first parenteral dose of 3-[5-amino-4-(3-cyanobenzoyl)-pyrazol-1-yl]-N-cyclopropyl-4-methylbenzamide is in the range of 30-60 mg, preferably 30 mg-50 mg, preferably 35 mg-45 mg, most preferably 40 mg.

In the descending dosage regimen referred to above, preferably the second parenteral dose of 3-[5-amino-4-(3-cyanobenzoyl)-pyrazol-1-yl]-N-cyclopropyl-4-methylbenzamide or a pharmaceutically acceptable derivative thereof, is in the range of 5 mg-40 mg, preferably 5 mg-30 mg, more preferably 10 mg-30 mg, most preferably 20 mg. Preferably the third parenteral dose of 3-[5-amino-4-(3-cyanobenzoyl)-pyrazol-1-yl]-N-cyclopropyl-4-methylbenzamide or a pharmaceutically acceptable derivative thereof, is in the range of 5 mg-40 mg, preferably 5 mg-30 mg, more preferably 10 mg-30 mg, most preferably 20 mg. Preferably the second and third doses are the same.

Preferably, the first parenteral dose of 3-[5-amino-4-(3-cyanobenzoyl)-pyrazol-1-yl]-N-cyclopropyl-4-methylbenzamide is about 40 mg, the second parenteral dose of 3-[5-amino-4-(3-cyanobenzoyl)-pyrazol-1-yl]-N-cyclopropyl-4-methylbenzamide is about 20 mg, and the third parenteral dose of 3-[5-amino-4-(3-cyanobenzoyl)-pyrazol-1-yl]-N-cyclopropyl-4-methylbenzamide is about 20 mg.

According to the kit embodiment of the invention, the individual dosage forms can be contained in one or more packages which are optionally labelled to indicate which order the dosage forms should be taken in. For example, a package or packages may be labelled "Dose 1", "Dose 2", and "Dose 3". Alternatively, the doses may be labelled "Day 1", "Day 3", "Day 5", or the like.

Preferably each dose within the composition, method or kit of the present invention is an immediate release formulation. The composition, method or kit of the present invention may comprise a larger first dose that is an immediate release formulation in order to quickly increase blood levels of 3-[5-amino-4-(3-cyanobenzoyl)-pyrazol-1-yl]-N-cyclopropyl-4-methylbenzamide, or a derivative thereof, followed by second and third doses that are both lower strength immediate release formulations.

It has surprisingly been found that the dosage regimens according to any aspect of the present invention are particularly effective for treating particular patient sub-populations suffering from an acute exacerbation of COPD, or at risk of developing an acute exacerbation of COPD. In particular, the patient population which has <2% blood eosinophils are considered steroid resistant, therefore resistant to standard of care treatment. The present invention finds particular advantage in successfully treating this patient population. Patients with high levels of sputum or blood eosinophils (defined by >2% of white cells in peripheral blood or >150 cells per microlitre blood) show good clinical response to corticosteroids, conversely those with blood eosinophils <2% (equivalent to about <150 white cells per microlitre) show resistance to systemic corticosteroids, have limited treatment options and therefore high unmet need (Bafadhel, McKenna, Terry, et al.: Biomarkers in COPD Exacerbations, 2011; American Journal Of Respiratory And Critical Care Medicine Vol 184, pp. 662-671; and Am J Respir Crit Care Med Vol 186, Iss. 1, pp 48-55, Jul. 1, 2012) and who are more responsive to anti-inflammatory treatment with corticosteroids (Singh et al, Eur Respir J 2014; 44: 1697-1700). Hence there is a long felt need for an effective treatment for this patient sub-population. The present invention is effective in treating patients with a blood eosinophil concentration of <2%.

Throughout this invention, the eosinophil level is expressed as percentage of white cells in peripheral blood. Thus, where it is stated that the human patients have <2% blood eosinophils, this is the percentage of white cells in peripheral blood.

In a further embodiment, the patient has not received 3-[5-amino-4-(3-cyanobenzoyl)-pyrazol-1-yl]-N-cyclopropyl-4-methylbenzamide therapy prior to initiation of the separate doses.

In an embodiment, the dosage regimen of the present invention may be used alone or may be used in combination with standard of care (SoC) treatment, which typically involves, but is not limited to use of steroids and/or β2-adrenergic agonists and/or muscarinic antagonists. Antibiotics may additionally be administered if the patient has an infection.

In an embodiment, the pharmaceutical composition is in the form of a dry powder formulation. In this embodiment, the doses are preferably administered from a dry powder inhaler.

In an embodiment, the pharmaceutical composition is in the form of an oral solid dosage form, preferably a tablet or a capsule.

In one embodiment, the pharmaceutical composition comprises one or more pharmaceutically acceptable excipients. Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When the composition of the invention is formulated as solid oral dosage form, it is preferably a capsule or a tablet. The following are preferably also contained in the capsule form of the invention:

Fillers and flow regulating agents, preferably in an amount of 5 to 60% by weight, related to the capsule weight. Fillers that may for example be considered are starches, celluoses, lactose, saccharose, fructose, sorbitol, mannitol, calcium phosphate, calcium carbonate, calcium sulphate, magnesium carbonate or magnesium oxide. 5-50% by weight are preferably used, relative to the capsule or tablet weight.

Flow regulating agents that may for example be considered are microcrystalline cellulose, lactose, polyglycols, starches, celluloses, talcum, talcum siliconisatum, calcium arachinate or calcium stearate, cetyl alcohol, stearyl alcohol, myristyl alcohol, stearic acid, lauric acid. Should the flow regulating agent not also serve as a filler, preferably 0.5-10% by weight are used hereof, relative to the capsule or tablet weight.

Disintegrants: use is for example made of alginates, starches (corn starch), pectins, carboxymethyl celluloses, polyvinylpolypyrrolidone, ultraamylopectin, betonite. Preferably 1-10% by weight are used, relative to the capsule or tablet weight.

Antiadhesion agents: use is for example made of glycols, talcum, talcum siliconisatum, talcum stearinicum, calcium stearate, aluminium stearate, stearic acid. Preferably, 0.1-10% by weight are used, relative to the capsule or tablet weight.

Binding agents: for example gelatin, cellulose ethers, amyloses pectins, cellulose, dextrose, polyglycols, tragacanth. Preferably, use is made of 0.1-80% by weight, relative to the capsule or tablet weight.

Tablets as well as capsules may be provided with a coating in known manner. It is possible to apply water-soluble, swellable, water insoluble or gastric juice resistant coatings which may be applied to the tablets or capsules from aqueous dispersion or solution or also from solution or dispersion in organic solvents such as for example ethanol, isopropanol, acetone, ether, dichloromethane or methanol.

When the composition of the invention is formulated as a dry powder formulation, in one embodiment the composition additionally comprises a force control agent.

A force control agent is an agent which reduces the cohesion between the fine particles within the powder formulation, thereby promoting deagglomeration upon dispensing of the powder from the dry powder inhaler.

Suitable force control agents are disclosed in WO 96/23485 and WO 2005/105043 and they typically consist of physiologically acceptable material, despite the fact that the material may not always reach the lung.

The force control agent may comprise a metal stearate, or a derivative thereof, for example, sodium stearyl fumarate or sodium stearyl lactylate. Advantageously, it comprises a metal stearate. For example, zinc stearate, magnesium stearate, calcium stearate, sodium stearate or lithium stearate. In one particular embodiment which may be mentioned, the additive material comprises or consists of magnesium stearate.

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina H R; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

When the composition of the invention is formulated as a dry powder formulation, in one embodiment the composition additionally comprises a carrier. In a further embodiment, the carrier comprises lactose, such as lactose monohydrate.

Oral liquid formulations of the invention may be in the form of oral solutions or suspensions. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of 3-[5-amino-4-(3-cyanobenzoyl)-pyrazol-1-yl]-N-cyclopropyl-4-methylbenzamide, and preferably from about 1 to 50% of 3-[5-amino-4-(3-cyanobenzoyl)-pyrazol-1-yl]-N-cyclopropyl-4-methylbenzamide.

When 3-[5-amino-4-(3-cyanobenzoyl)-pyrazol-1-yl]-N-cyclopropyl-4-methylbenzamide, or derivative thereof, is administered by intravenous or subcutaneous injection, 3-[5-amino-4-(3-cyanobenzoyl)-pyrazol-1-yl]-N-cyclopropyl-4-methylbenzamide or the derivative will be in the form of a parenterally acceptable aqueous solution. The preparation of such parenterally acceptable solutions, having due regard to pH, isotonicity, stability, and the like, is within the skill in the art. A preferred pharmaceutical composition for intravenous or subcutaneous injection should contain, in addition to 3-[5-amino-4-(3-cyanobenzoyl)-pyrazol-1-yl]-N-cyclopropyl-4-methylbenzamide or a pharmaceutically acceptable derivative thereof, an isotonic vehicle such as sodium chloride Injection, Ringer's Injection, dextrose Injection, dextrose and sodium chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer.

For transmucosal administration, penetrants appropriate to the barrier to be permeated are used in the formulation. Such penetrants are generally known in the art.

The formulations of the present invention may include 3-[5-amino-4-(3-cyanobenzoyl)-pyrazol-1-yl]-N-cyclopropyl-4-methylbenzamide as the only pharmaceutically active agent. Alternatively, the formulations may include one or more further active agents. The additional active agents may include, for example:

1) steroid drugs such as, for example, alcometasone, beclomethasone, beclomethasone dipropionate, betamethasone, budesonide, clobetasol, deflazacort, diflucortolone, desoxymethasone, dexamethasone, fludrocortisone, flunisolide, fluocinolone, fluometholone, fluticasone, fluticasone proprionate, fluticasone furoate, mometasone furoate, hydrocortisone, triamcinolone, nandrolone decanoate, neomycin sulphate, rimexolone, methylprednisolone and prednisolone;

2) antibiotic and antibacterial agents such as, for example, metronidazole, sulphadiazine, triclosan, neomycin, amoxicillin, amphotericin, clindamycin, aclarubicin, dactinomycin, nystatin, mupirocin and chlorhexidine;

3) systemically active drugs such as, for example, isosorbide dinitrate, isosorbide mononitrate, apomorphine and nicotine;

4) antihistamines such as, for example, azelastine, chlorpheniramine, astemizole, cetitizine, cinnarizine, desloratadine, loratadine, hydroxyzine, diphenhydramine, fexofenadine, ketotifen, promethazine, trimeprazine and terfenadine;

5) anti-inflammatory agents such as, for example, piroxicam, benzydamine, diclofenac sodium, ketoprofen, ibuprofen, heparinoid, nedocromil, sodium cromoglycate, fasafungine and iodoxamide;

6) antimuscarinic/anticholinergic agents such as, for example, atropine, benzatropine, biperiden, cyclopentolate, oxybutinin, orphenadine hydrochloride, procyclidine, propantheline, propiverine, tiotropium, tropicamide, trospium, ipratropium bromide, GSK573719 and oxitroprium bromide;

7) bronchodilators, such as salbutamol, fenoterol, formoterol, indacaterol, vilanterol and salmeterol;

8) sympathomimetic drugs, such as adrenaline, noradrenaline, dexamfetamine, dipirefin, dobutamine, dopexamine, phenylephrine, isoprenaline, dopamine, pseudoephedrine, tramazoline and xylometazoline;

9) opiates, such as for pain management, such as, for example, buprenorphine, dextromoramide, diamorphine, codeine phosphate, dextropropoxyphene, dihydrocodeine, papaveretum, pholcodeine, loperamide, fentanyl, methadone, morphine, oxycodone, phenazocine, pethidine and combinations thereof with an anti-emetic;

10) analgesics and drugs for treating migraine such as clonidine, codine, coproxamol, dextropropoxypene, ergotamine, sumatriptan, tramadol and non-steroidal anti-inflammatory drugs;

11) pharmaceutically acceptable salts of any of the foregoing.

Preferably, when 3-[5-amino-4-(3-cyanobenzoyl)-pyrazol-1-yl]-N-cyclopropyl-4-methylbenzamide is coadministered or added to treatments using other active ingredients, such other active ingredients are preferably selected from steroid drugs, antibiotics, and mixtures thereof.

All stereoisomers of 3-[5-amino-4-(3-cyanobenzoyl)-pyrazol-1-yl]-N-cyclopropyl-4-methylbenzamide are contemplated, either in admixture or in pure or substantially pure form. 3-[5-amino-4-(3-cyanobenzoyl)-pyrazol-1-yl]-N-cyclopropyl-4-methylbenzamide as used herein embraces all the possible stereo isomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. 3-[5-amino-4-(3-cyanobenzoyl)-pyrazol-1-yl]-N-cyclopropyl-4-methylbenzamide may also have prodrug forms. Any compound that will be converted in vivo to provide the bioactive agent is a prodrug. Various forms of prodrugs are well known in the art.

Terms

Unless defined otherwise, all technical and scientific terms used herein have the same meaning as is commonly understood by one of skill in the art to which the invention(s) belong.

Terms used in the specification have the following meanings:

"Chronic obstructive pulmonary disease" or "COPD" as used herein is a common preventable and treatable disease that is characterised by persistent airflow limitation that is usually progressive and associated with an enhanced chronic inflammatory response in the airways and the lung to noxious particles of gases. Characteristic symptoms of the disease include dyspnea, chronic cough and chronic sputum production.

"Acute exacerbations of chronic obstructive pulmonary disease" or "AECOPD" as used herein mean a sudden worsening of any of the symptoms of the chronic obstructive pulmonary disease, typically involving decreased airflow and increased lung hyperinflation versus stable COPD. Acute exacerbations generally have a substantial negative impact on the well-being of patients and typically require the patient to receive urgent medical treatment in a hospital in an attempt to return the patient to the previously stable disease state.

"Reoccurrence of an acute exacerbation of COPD" as used herein means an occurrence of an acute exacerbation of COPD that the patient suffers at least 15 days after the last dose of 3-[5-amino-4-(3-cyanobenzoyl)-pyrazol-1-yl]-N-cyclopropyl-4-methylbenzamide in the first (or second, third, nth) administration to treat a first (or second, third, nth) acute exacerbation of COPD. Accordingly, prevention of a reoccurrence of an acute exacerbation of COPD means that the patient does not suffer from an occurrence of an acute exacerbation of COPD 15 days or greater subsequent the last dose of 3-[5-amino-4-(3-cyanobenzoyl)-pyrazol-1-yl]-N-cyclopropyl-4-methylbenzamide in the first (or second, third, nth) administration to treat a first (or second, third, nth) acute exacerbation of COPD.

"Treatment failure of an acute exacerbation of COPD" as used herein means a worsening of any of the symptoms of the chronic obstructive pulmonary disease—typically involving decreased airflow and increased lung hyperinflation versus stable COPD—within 14 days after the last dose of 3-[5-amino-4-(3-cyanobenzoyl)-pyrazol-1-yl]-N-cyclopropyl-4-methylbenzamide in the administration, which results in the patient having to receive further treatment for the acute exacerbation of COPD.

"Pharmaceutically acceptable derivative" as used herein means a derivative of the therapeutically active compound in question that is suitable for use as an active ingredient of a pharmaceutical product.

"Forced Expiratory Volume in One Second" or "$FEV_1$" as used herein is the volume of air that can forcibly be blown out in one second, after full inspiration, which is measured by a spirometer. It is a measure of lung function or performance. Average values for $FEV_1$ in healthy people depend mainly on sex and age. Values of between 80% and 120% of the average value are considered normal.

"p38α" as used herein refers to the enzyme disclosed in Han et al. (1995) *Biochim. BioPhys. Acta* 1265(2-3):224-7.

"p38β" as used herein refers to the enzyme disclosed in Jiang et al. (1996) *J. Biol. Chem.* 271 (30):17920-6.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The entire disclosure of each international patent application mentioned in this patent specification is fully incorporated by reference herein for all purposes.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

Hereafter, reference to 3-[5-amino-4-(3-cyanobenzoyl)-pyrazol-1-yl]-N-cyclopropyl-4-methylbenzamide will include reference to the compound per se and pharmaceutically acceptable derivatives thereof.

As used herein, pharmaceutically acceptable derivatives of 3-[5-amino-4-(3-cyanobenzoyl)-pyrazol-1-yl]-N-cyclopropyl-4-methylbenzamide include salts, esters, enol ethers, enol esters, acetals, ketals, orthoesters, hemiacetals, hemiketals, acids, bases, solvates or hydrates. Such derivatives may be readily prepared by those of skill in this art using known methods for such derivatization.

Pharmaceutically acceptable salts of 3-[5-amino-4-(3-cyanobenzoyl)-pyrazol-1-yl]-N-cyclopropyl-4-methylbenzamide include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, oxalates, benzoates, salicylates, maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable solvates and hydrates of 3-[5-amino-4-(3-cyanobenzoyl)-pyrazol-1-yl]-N-cyclopropyl-4-methylbenzamide are complexes of a compound with one or more solvent or water molecules, or 1 to about 100, or 1 to about 10, or one to about 2, 3 or 4, solvent or water molecules.

In particular the term derivatives covers pharmaceutically acceptable salts, solvates and hydrates of 3-[5-amino-4-(3-cyanobenzoyl)-pyrazol-1-yl]-N-cyclopropyl-4-methylbenzamide.

Additional embodiments and features are set forth in part in the description that follows, and in part will become apparent to those skilled in the art upon examination of the specification or may be learned by the practice of the invention. This invention is further illustrated by the following example which should not be construed as limiting.

Example 1

BCT197 is currently prepared as hard gelatin capsules of 1 mg, 5 mg, 7 mg, 10 mg and 20 mg, 25 mg and 50 mg for oral administration. The hard gelatin capsules contain a white to off-white powder in a pink opaque hard gelatin capsule. The following excipients used for the capsules are standard excipients of compendial quality: lactose monohydrate, sodium starch glycolate, povidone, colloidal silicon dioxide, magnesium stearate.

The manufacturing processes involve standard pharmaceutical processes of mixing and filling. The 1 mg and 10 mg hard gelatin capsules are packaged in HDPE bottles with induction seals and child-resistant caps. The 5 mg, 25 mg and 50 mg hard gelatin capsules can be packaged either in Aclar blisters or HDPE bottles with induction seals and child-resistant caps. The 7 mg and 20 mg hard gelatin capsules are packaged only in Aclar blisters.

Example 2

A Phase 2 trial (referred to as AETHER) was a double-blind, randomised, placebo-controlled clinical study investigating the use of BCT-197, on top of Standard of Care, for the treatment of patients with AECOPD. Standard of Care included the addition of steroids and/or antibiotics to a patient's chronic COPD medication and symptomatic bronchodilators. Following baseline assessment, 282 eligible patients were randomised to receive either one of two different dose regimens of BCT-197 or placebo (three doses over five days).

The trial assessed adult patients ≥40 years with an acute exacerbation of COPD (as defined by increase in symptoms of cough, and/or sputum and/or breathlessness that required addition of antibiotics and or systemic corticosteroids to their regular treatment).

The dosing regimen of 3-[5-amino-4-(3-cyanobenzoyl)-pyrazol-1-yl]-N-cyclopropyl-4-methylbenzamide or matching oral placebo administered are shown in Table 1.

TABLE 1

Study Dosing Schedules

| | Day 1 | Day 3 | Day 5 |
|---|---|---|---|
| Regimen 1 (High) | 75 mg | 40 mg | 40 mg |
| Regimen 2 (Low) | 40 mg | 20 mg | 20 mg |
| Regimen 3 | Placebo | Placebo | Placebo |

BCT197 or placebo was added on top of the standard of care for the exacerbation. Exploratory long term outcomes after the acute treatment were included out to 6 months. These showed that a short course of high dose BCT 197 over 5 days was able to reduce the occurrence of new exacerbations that require hospitalisation by 40-60% for the subsequent 6 months (FIG. 1), with the greatest effect between 3 and 4 months (based on numerical difference to placebo and statistical significance).

Figure 2:
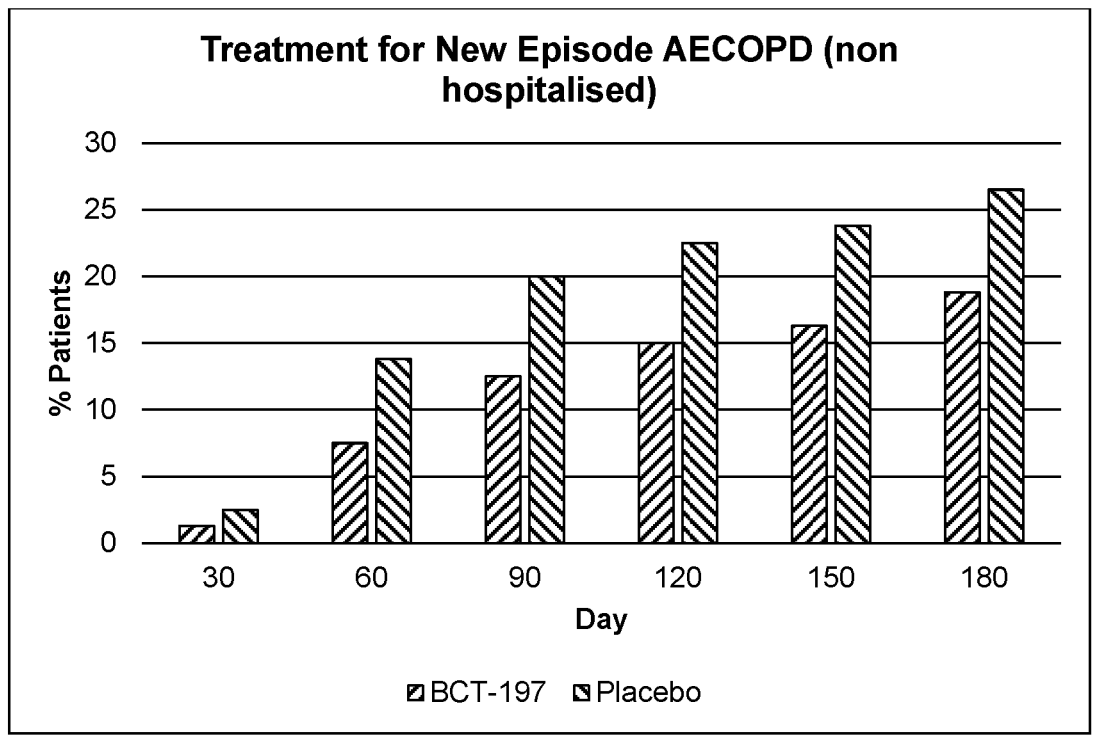
FIG. 2: Occurrence of new acute exacerbations of COPD that did not require hospitalisation.

The effect was also observed on recurrent exacerbations that were not hospitalised with reductions by the short course of treatment with high dose BCT197 (FIG. 2).

Figure 3:
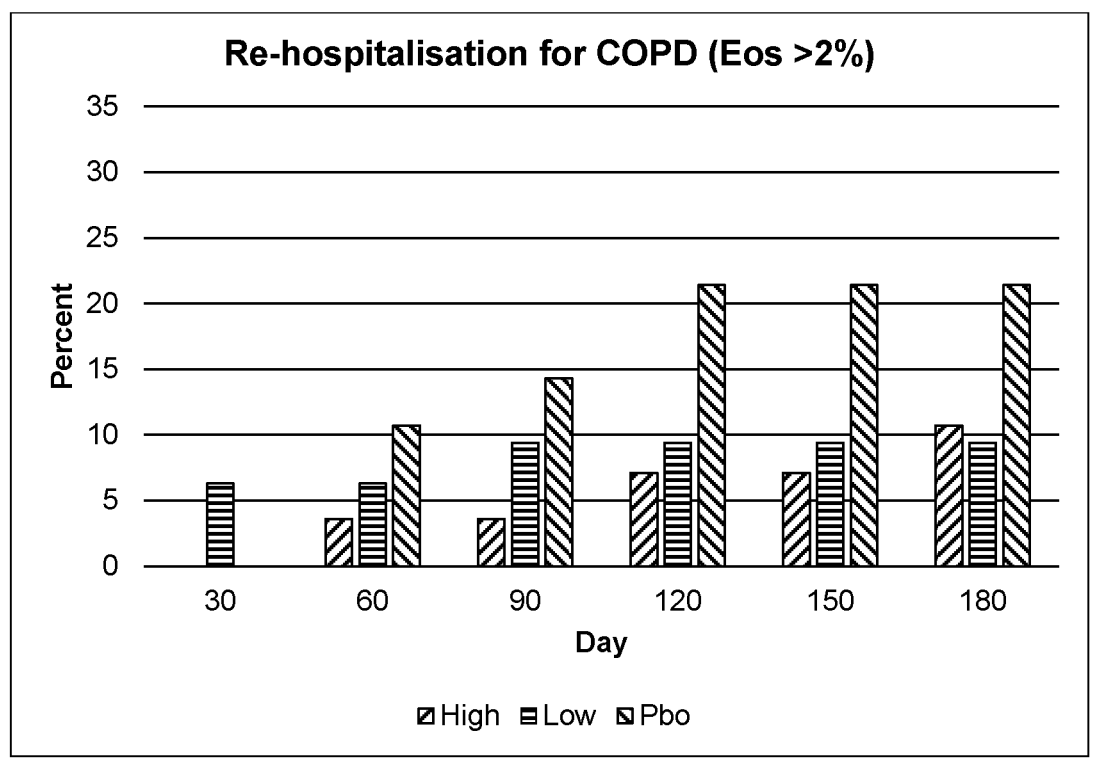
FIG. 3: Occurrence of new acute exacerbations of COPD that required re-hospitalisation in the high eosinophil sub group (Eos>2%).

These data also showed that a short course of both high and low dose BCT 197 over 5 days was able to reduce re-hospitalisation for COPD for the subsequent 6 months in the high eosinophil sub group (Eos>2%) versus placebo (FIG. 3).

Figure 4:
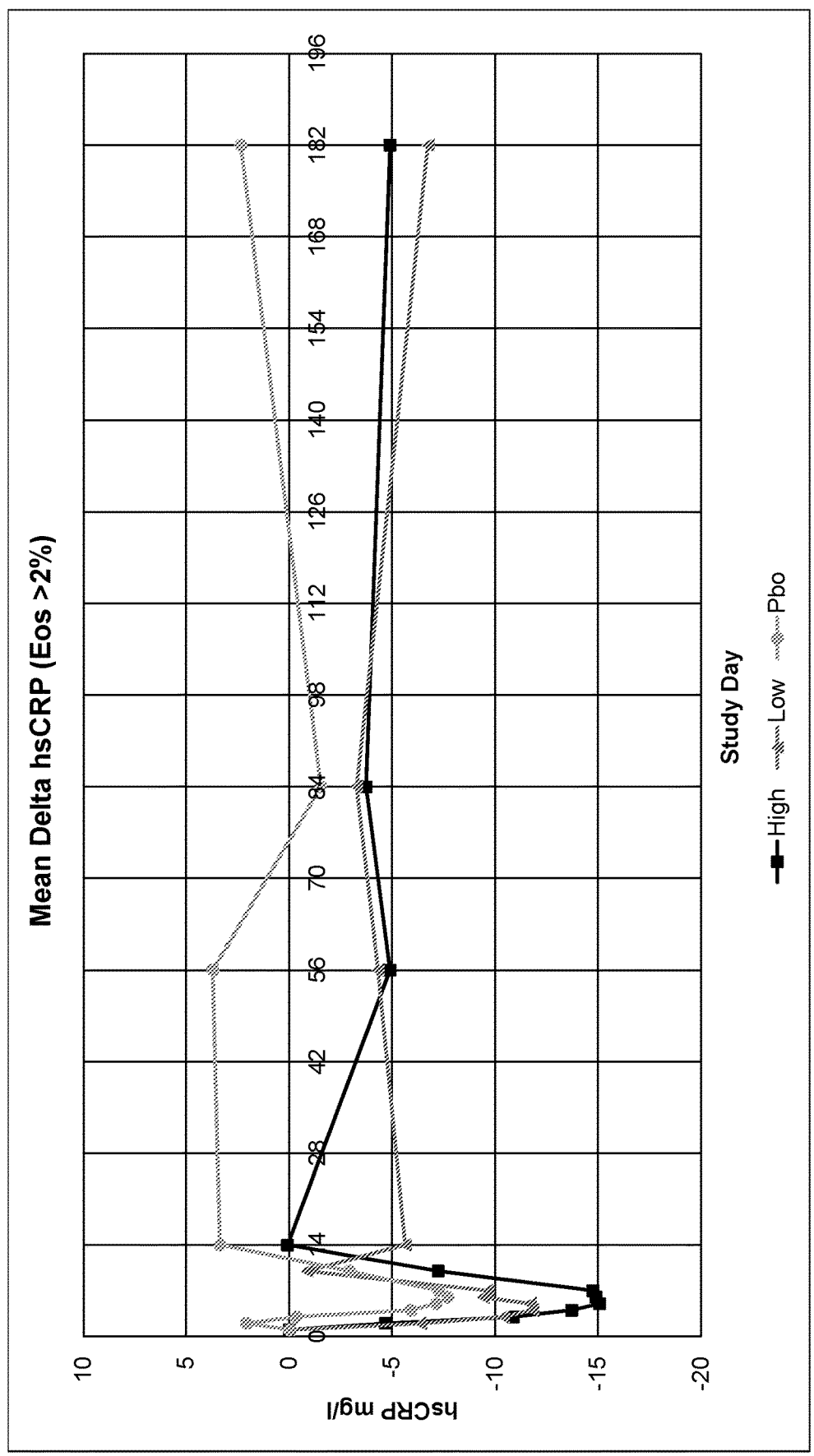
FIG. 4: Mean difference in high sensitivity C-Reactive Protein (hsCRP) blood concentration in the high eosinophil sub group (Eos>2%).
Figure 5:
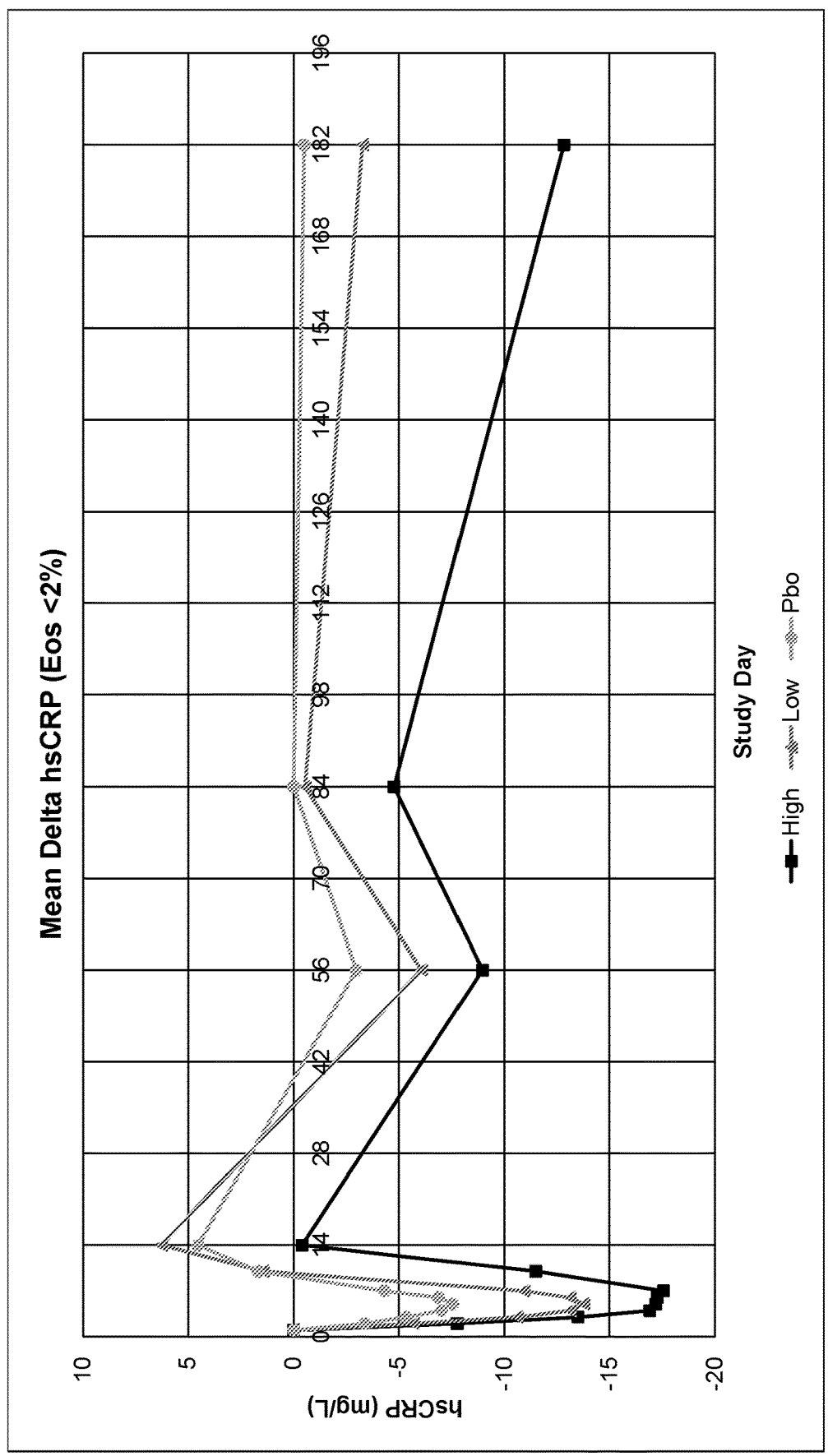
FIG. 5: Mean difference in hsCRP blood concentration in the <2% eosinophil group (Eos<2%).

Inflammatory biomarkers are related to disease outcomes (Barnes and Celli, Eur Respir J, 2009, 33, pp 1165-1185; Bourdin et al., Eur Respir Rev, 2009, 18, pp 198-212) and are central to the proposed mechanism of action for BCT197. A further exploratory outcome was included out to 6 months, namely the inflammatory biomarker high sensitivity C-Reactive Protein (hsCRP) measured in patients. Patients treated with both high and low dose BCT 197 over 5 days showed a sustained and durable reduction in hsCRP for the subsequent 6 months versus placebo in both high and low eosinophil sub group (FIGS. 4 and 5). This is supportive that treatment in accordance with the invention leads to a reduction in re-hospitalisations and non-hospitalised exacerbations over this period through long term reduction in inflammation.

Figure 6:
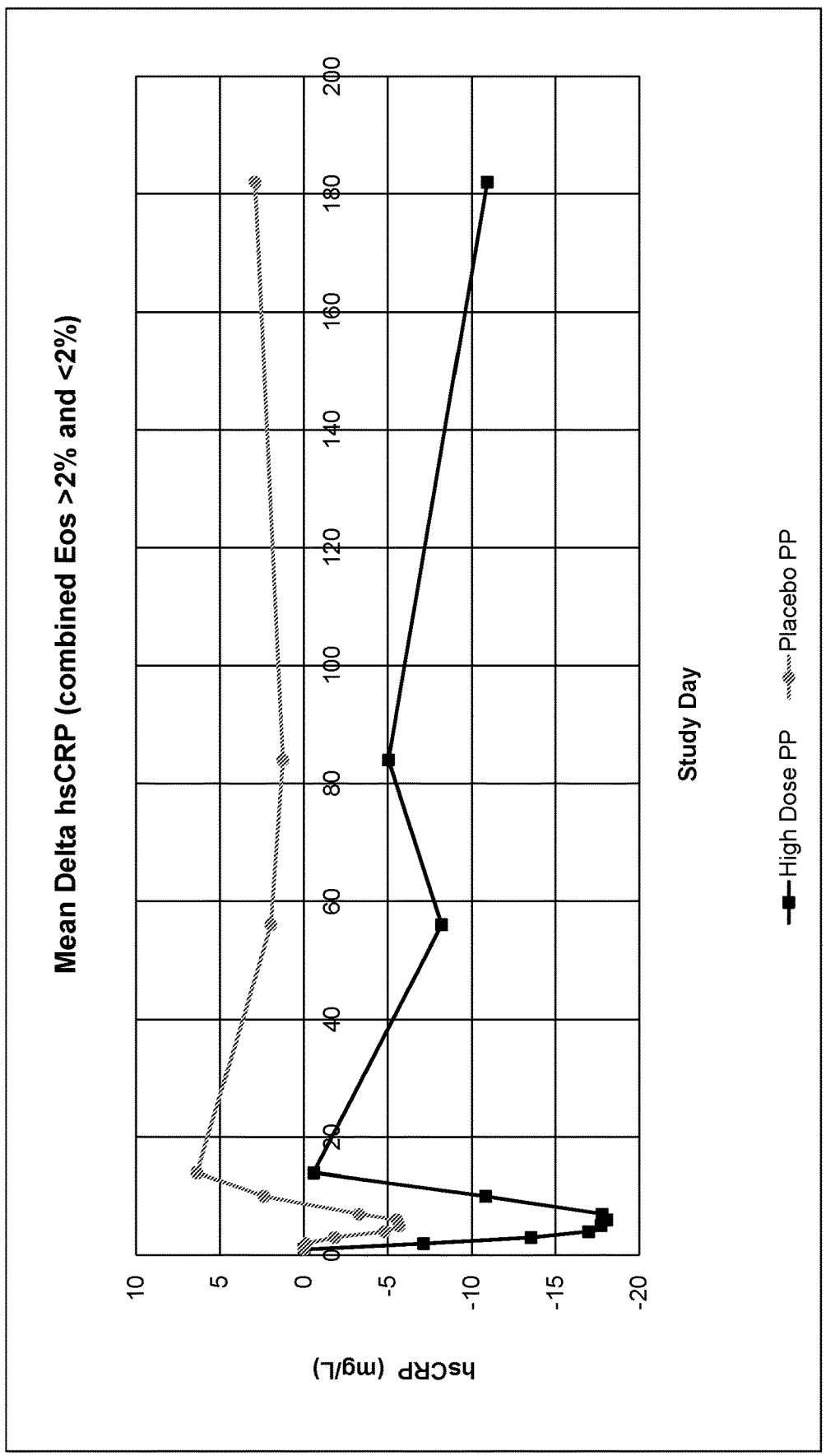
FIG. 6: Mean difference in hsCRP blood concentration with the subpopulations combined (combined Eos>2% and <2%).

FIG. 6 further demonstrates the change from baseline in hsCRP in patients treated with high dose BCT197 and placebo. A rapid decrease in hsCRP to day 7 during acute treatment is shown which is significantly greater in the BCT197 treated group compared to placebo (p<0.05 at Day 3, 7 and 10). After the acute treatment period, the hsCRP remains lower in those who had received BCT197 compared to placebo to Day 180 (p value<0.05) without additional dosing of BCT197, supporting a prolonged pharmacology effect on inflammation by BCT197.

The effect of BCT197 on suppression of hsCRP over the acute AECOPD treatment is an important observation for understanding the long term benefit of the treatment of the present invention, as end of treatment hsCRP has been shown to be predictive of time to next exacerbation (Perera et al., Eur Respir J, 2007, 29, pp 527-534). The dose-related effects on hsCRP were also present out to 6 months after BCT197 systemic exposure, suggesting treatment may have led to a change in the underlying level of systemic inflammation.

Figure 7:
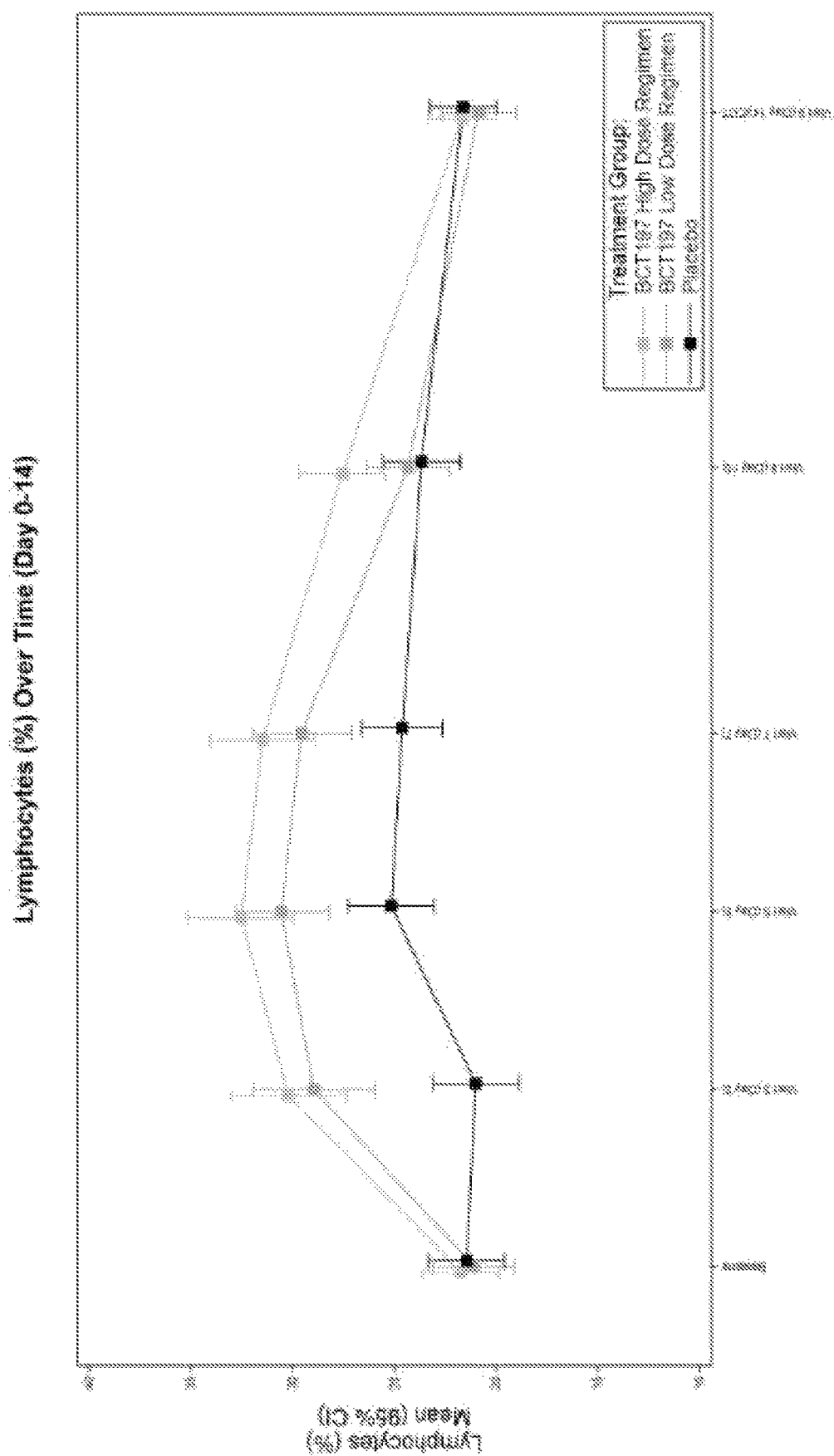
FIG. 7: Change in lymphocyte blood concentration to day 14.
Figure 8:
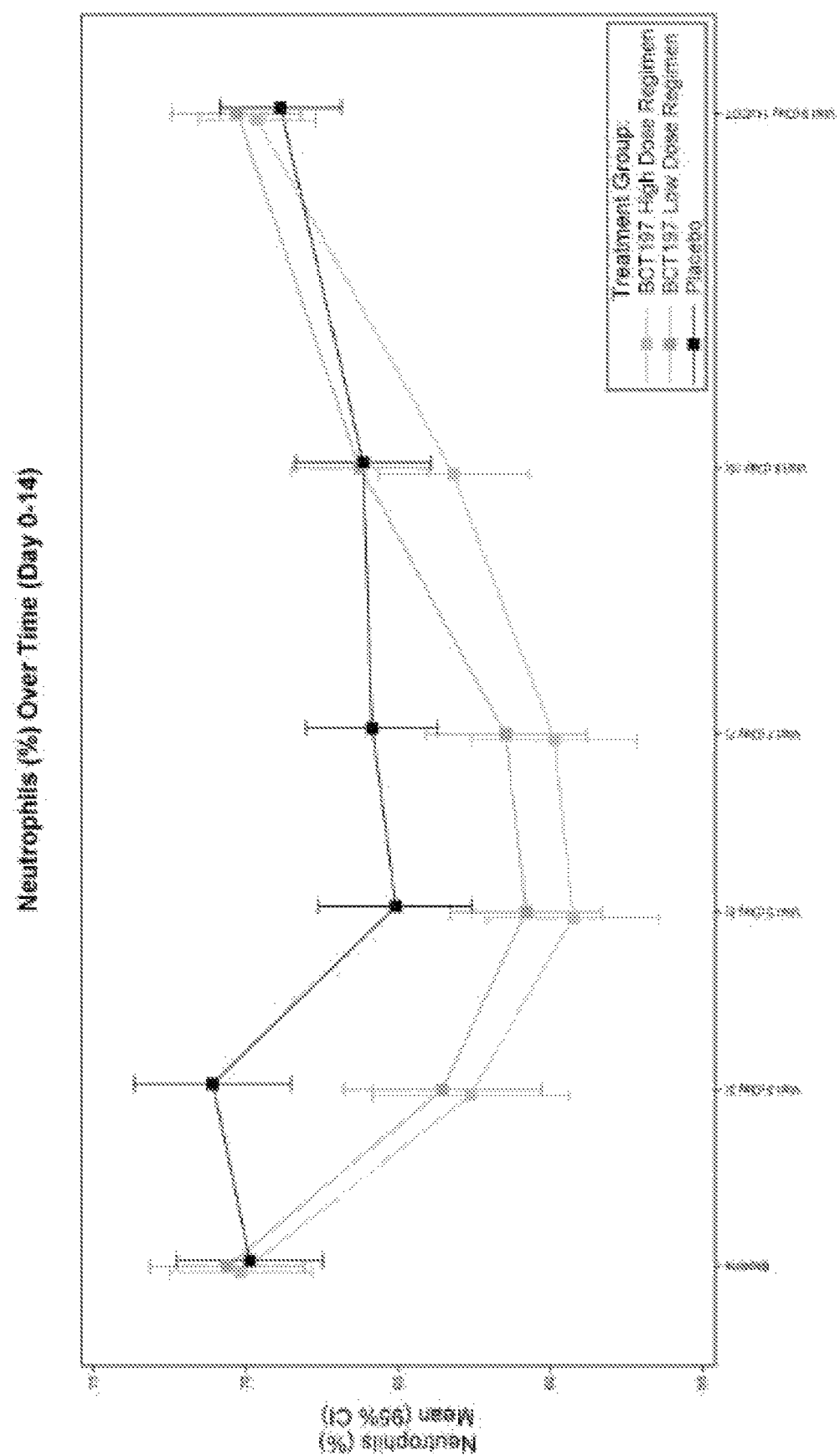
FIG. 8: Change in neutrophil blood concentration to day 14.

FIGS. 7 and 8 demonstrate the change from baseline in % lymphocytes and neutrophils measured in patients treated with BCT197 (High Dose and Low Dose) versus Placebo and follow-up to Day 14 for lymphocytes and Day 56 (Week 8) for neutrophils. A rapid decrease in % neutrophils during acute treatment is shown, which is greater in the BCT197 treated group compared to placebo with dose-dependent effect (FIG. 8). Conversely a dose-dependent increase in lymphocytes over the acute treatment period is shown (FIG. 7).

Figure 9:
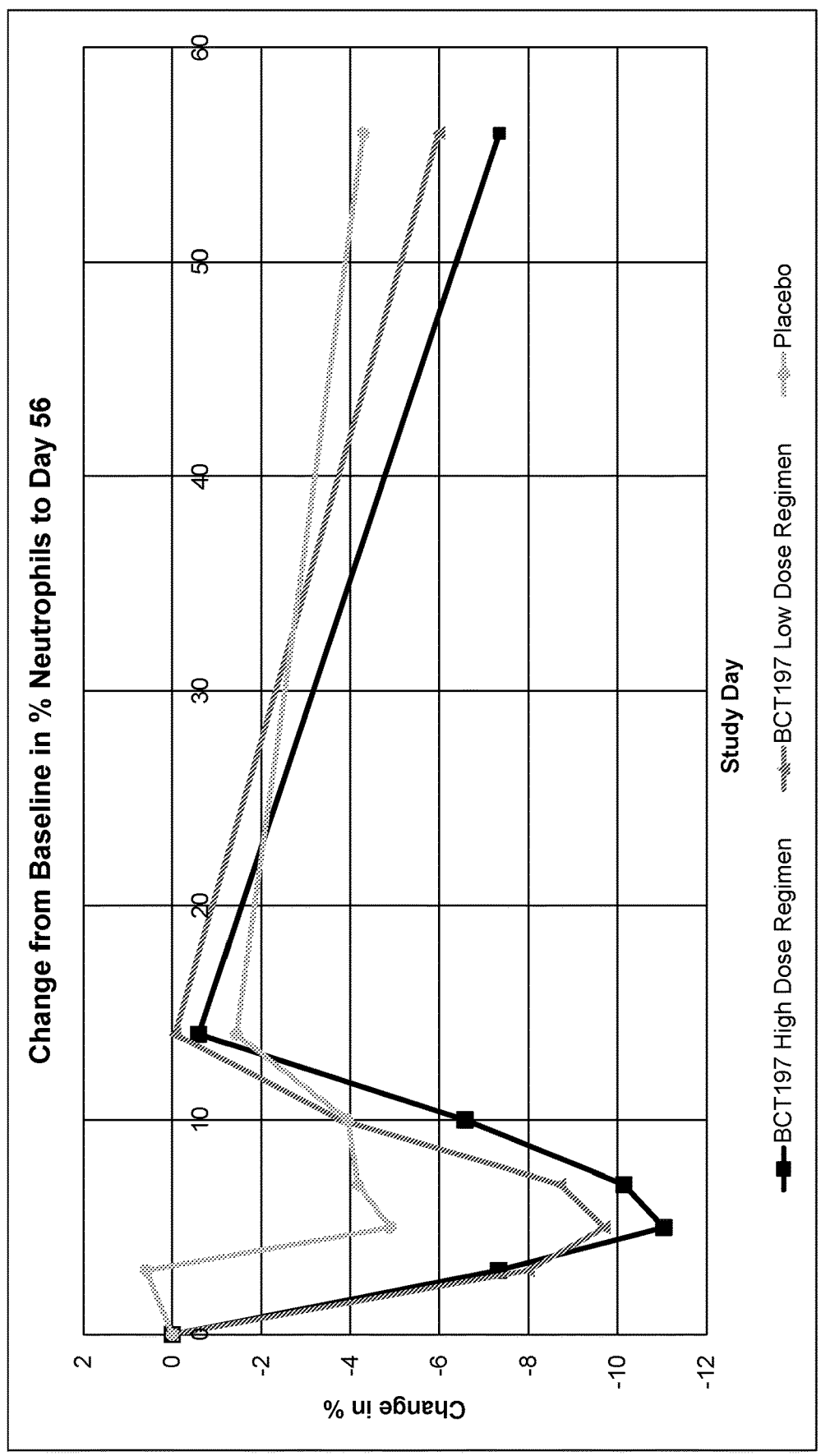
FIG. 9: Difference from baseline in neutrophil blood concentration to day 56.

Systemic markers of adaptive and innate immunity are predictive of disease progression in COPD. A mixed pattern of lymphocyte suppression and enhanced myeloid (neutrophil) response, reflected in absolute levels (increased levels of neutrophils and decreased lymphocytes) in peripheral blood have been shown to be independent predictors in predictive models of lung function in COPD. The reduction in % neutrophils remains greater in those who had received BCT197 compared to placebo to Day 56 (FIG. 9) without additional dosing of BCT197, supporting a prolonged pharmacology effect on inflammation by BCT197. Consequently, the effect of BCT197 to rebalance these biomarkers to a healthier phenotype, including beyond the period of systemic drug exposure, supports the potential benefit of the dosing regimens of the present invention.

Thus a treatment course of BCT197 over 5 or 7 days could be used to prevent or reduce recurrent exacerbations of COPD. The durability of the response supports repeat courses to be given outside an acute exacerbation during stable disease state.

Preferably, the repeat courses would preferably be given about every 12 weeks (measured from the start of the adjacent courses), but could be given at intervals from every 4 weeks to every 6 months.

Moreover, the rapid decrease in neutrophils and rapid increase in lymphocytes in patients treated with BCT197 supports that a treatment course of BCT197 over 5 or 7 days could be used to prevent treatment failures of exacerbations of COPD.

Inclusion criteria for the study population were:
Males/females≥40
On regular treatment for COPD (categories C and D by 2015 GOLD guidelines)
Presence of an active exacerbation of the ongoing COPD requiring hospitalisation for treatment:
At least one moderate or severe COPD exacerbation in the preceding 12 months
Smoking history of at least 10 pack years
FEV1<65% of the predicted normal value
Exclusion criteria for the study population were:
Current diagnosis of asthma
Treatment with systemic corticosteroids or antibiotics in the prior 4 weeks.
Requiring intensive care unit treatment
Clinically significant cardiovascular condition of clinically significant ECG abnormality
Concurrent pneumonia, pulmonary embolus or pneumothorax Example 3

A Phase 2 trial (referred to as AETHER) was a double-blind, randomised, placebo-controlled clinical study investigating the use of BCT-197, on top of Standard of Care, for the treatment of patients with AECOPD. Standard of Care included the addition of steroids and/or antibiotics to a patient's chronic COPD medication and symptomatic bronchodilators. Following baseline assessment, 282 eligible patients were randomised to receive either two different dose regimens of BCT-197 or placebo (three doses over five days). The primary endpoint was a comparison of change in forced expiratory volume in 1 second (FEV1) from baseline to day 7 within each arm of the study.

The trial assessed adult patients≥40 years with an acute exacerbation of COPD (as defined by increase in symptoms of cough, and/or sputum and/or breathlessness that required addition of antibiotics and or systemic corticosteroids to their regular treatment).

Patients received one of two oral dosing regimens of 3-[5-amino-4-(3-cyanobenzoyl)-pyrazol-1-yl]-N-cyclopropyl-4-methylbenzamide or matching oral placebo administered according to the dosing schedules shown in Table 2.

TABLE 2

Study Dosing Schedules

|  | Day 1 | Day 3 | Day 5 |
| --- | --- | --- | --- |
| Regimen 1 (High) | 75 mg | 40 mg | 40 mg |
| Regimen 2 (Low) | 40 mg | 20 mg | 20 mg |
| Regimen 3 | Placebo | Placebo | Placebo |

Inclusion criteria for the study population were:
Males/females≥40
On regular treatment for COPD (categories C and D by 2015 GOLD guidelines)
Presence of an active exacerbation of the ongoing COPD requiring hospitalisation for treatment:
At least one moderate or severe COPD exacerbation in the preceding 12 months
Smoking history of at least 10 pack years
FEV1<65% of the predicted normal value
Exclusion criteria for the study population were:
Current diagnosis of asthma
Treatment with systemic corticosteroids or antibiotics in the prior 4 weeks.
Requiring intensive care unit treatment
Clinically significant cardiovascular condition of clinically significant ECG abnormality
Concurrent pneumonia, pulmonary embolus or pneumothorax Efficacy of treatment was measured by the primary endpoint of change in FEV1 from baseline (before treatment) to Day 7. Patients with COPD and low eosinophils (determined by blood percentages or absolute counts) are considered to be poorly responsive to treatment of acute exacerbations using known treatments.

Blood having an eosinophil percentage greater than or equal to 2% is used to characterise patients with COPD with eosinophilic lung inflammation (Bafadhel, McKenna, Terry, et al.: Biomarkers in COPD Exacerbations, 2011; AMERICAN JOURNAL OF RESPIRATORY AND CRITICAL CARE MEDICINE VOL 184, pp.

662-671) and who are more responsive to anti-inflammatory treatment with corticosteroids (Singh et al, Eur Respir J 2014; 44: 1697-1700). The present invention is effective in treating patient with a blood eosinophil concentration of <2%. Such patients are considered to be resistant to treatment with standard of care for COPD. Hence there is a long felt need for an effective treatment for this patient sub-population.

Figure 10:
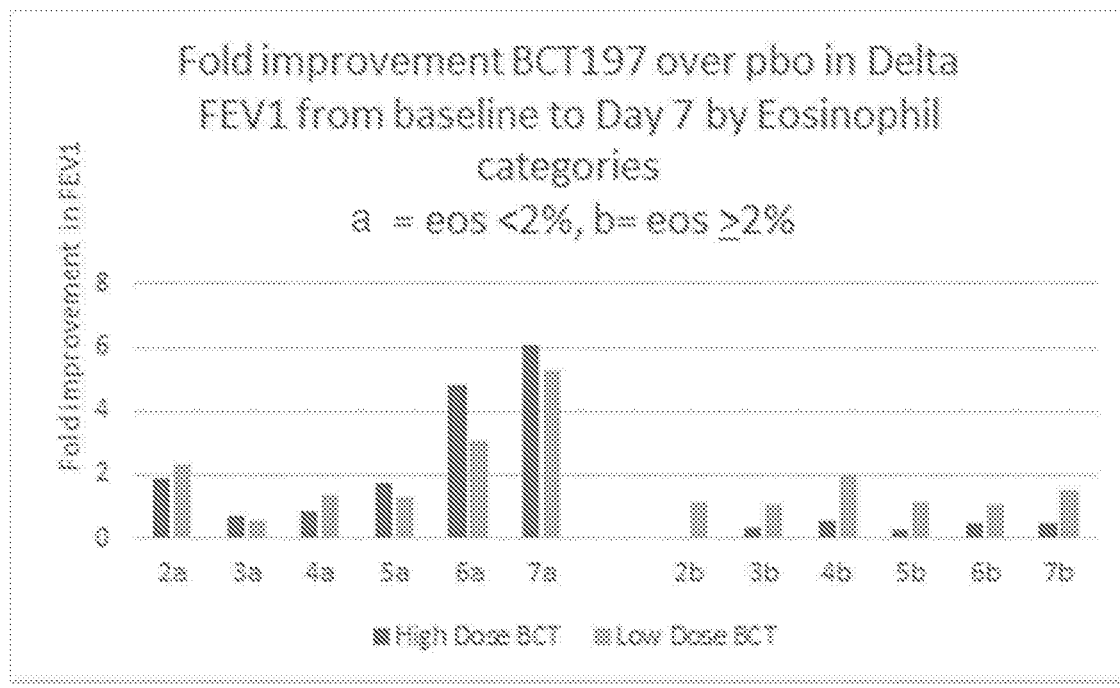
FIG. 10: Shows a comparison of responses to treatment with 3-[5-amino-4-(3-cyanobenzoyl)-pyrazol-1-yl]-N-cyclopropyl-4-methylbenzamide within the >2% eosinophil sub-population (left hand side 'a' is eosinophil count <2%, right had side eosinophil count 'b; >2%).

When treatment took place with BCT197, a sub-group analysis of those with blood eosinophils <2%, surprisingly showed a substantial and consistent improvement in FEV1 compared to other sub-groups. This is shown in FIG. 10 below. As expected patients treated with standard of care and placebo showed no improvement in FEV1.

The data support that patients with eosinophils <2% represent a specific sub-group of COPD patients who are responsive to BCT197 treatment.

This shows that there is a sub-population of COPD sufferers (identified by baseline eosinophil count) that does not respond to standard of care (i.e. those given standard of care and placebo show no improvement in FEV1) and where compound A results in significant improvement within that sub-population. Thus the present invention provides efficacy in defined sub-population that is resistant to standard of care treatment.

FIG. 10 shows a comparison of responses with the >2% eosinophil sub-population (left hand side 'a' is eosinophil count <2%, right had side eosinophil count 'b; >2%). It can be seen that the response to standard of care alone (as reflected in the placebo arm) is good and the relative difference that BCT197 makes to standard of care is much less than in the low eosinophil group.

Figure 11:
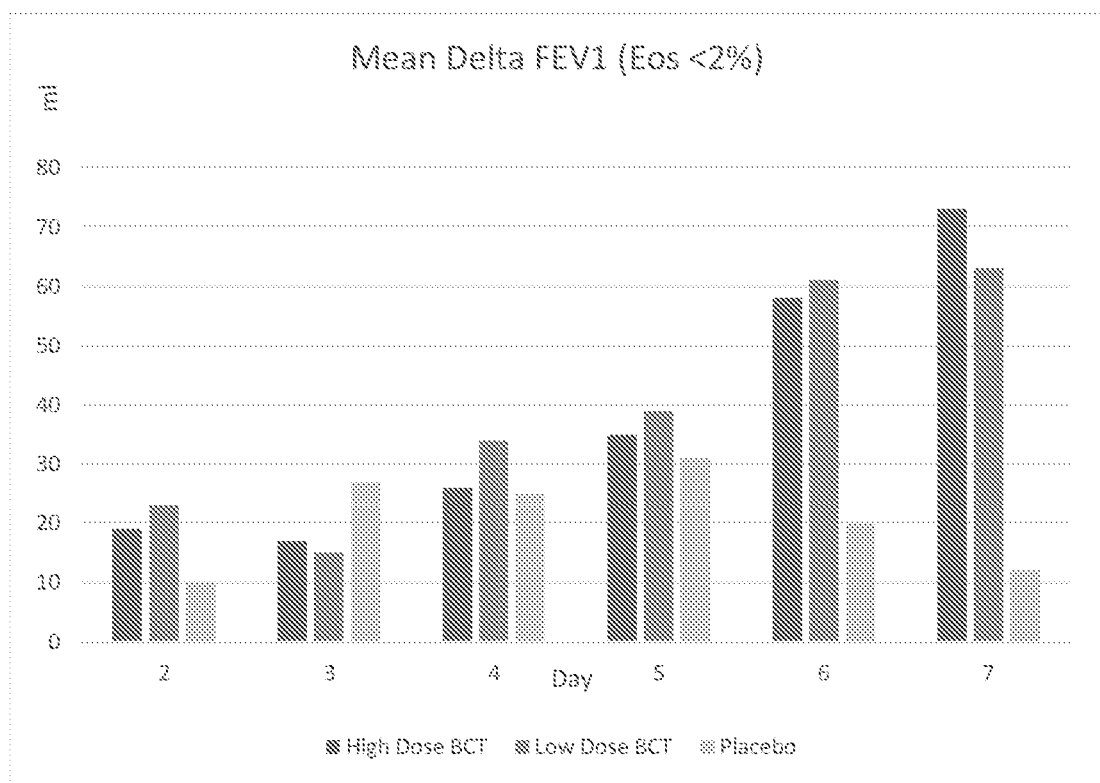
FIG. 11: Shows a comparison in FEV1 from baseline to Day 7 for a high dose regimen, low dose regimen and placebo.

FIG. 11 shows a comparison in FEV1 from baseline to Day 7 within each arm of the study. Placebo plus Standard of Care showed insignificant improvement in the low blood eosinophil (<2%) group.

A further exploratory outcome included over the treatment period to Day 5 and BCT197 systemic exposure (to Day 14) were the inflammatory biomarkers high sensitivity C-Reactive Protein (hsCRP) and fibrinogen measured in patient blood. Patients treated with high and low dose BCT197 over 5 days showed a dose-dependent reduction versus placebo in hsCRP and fibrinogen from baseline including in patient populations with <2% eosinophils. This was maximal at Day 7 (FIGS. 12 and 13) coincident with the highest improvement in FEV1 (FIG. 11) in response to BCT197 in the same patient population with <2% eosinophils.

Figure 12:
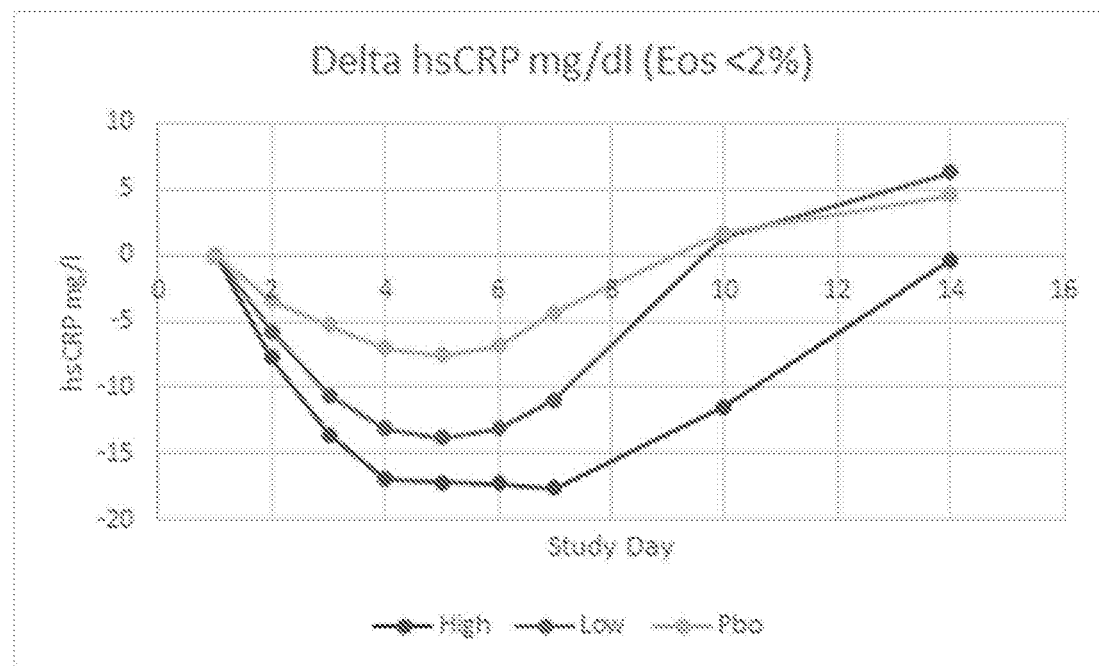
FIG. 12: Shows difference in high sensitivity C-Reactive Protein (hsCRP) blood concentration in patients with an acute exacerbation of COPD with a blood eosinophil count of <2% (Eos<2%).
Figure 13:
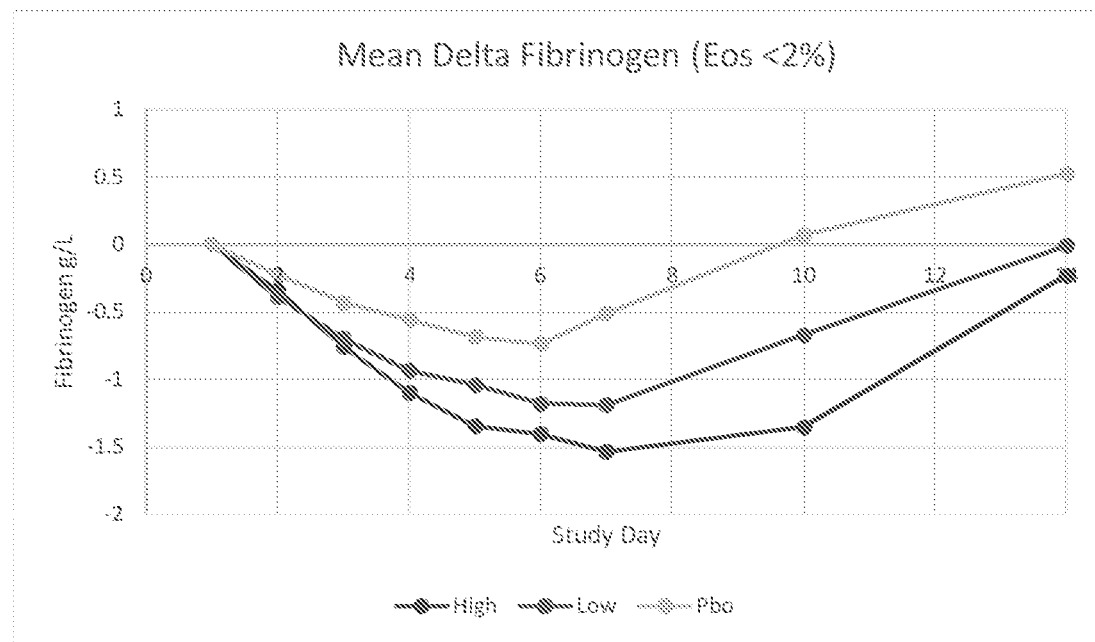
FIG. 13: Shows difference in fibrinogen blood concentration in patients with an acute exacerbation of COPD with a blood eosinophil count of <2% (Eos<2%).

These data in FIGS. 12 and 13 show a dose-dependent reduction in the inflammatory blood biomarkers hsCRP and fibrinogen. This shows that BCT197 is able to suppress inflammation, over and above the Standard of Care that all patients were receiving, including in low eosinophil populations that are considered treatment resistant and gives mechanistic support to the physiological benefit in FEV1 observed over the same time period.

The subgroup would be defined as patients with an acute exacerbation of COPD with a blood eosinophil count of <2%.

The following represent numbered disclosures.

One. A pharmaceutical composition comprising 3-[5-amino-4-(3-cyanobenzoyl)-pyrazol-1-yl]-N-cyclopropyl-4-methylbenzamide for use in the treatment of acute exacerbations of chronic obstructive pulmonary disease in human patients having <2% blood eosinophils.

Two. A method for the treatment of acute exacerbations of chronic obstructive pulmonary disease which comprises administering to a human patient having <2% blood eosinophils, an effective amount of 3-[5-amino-4-(3-cyanobenzoyl)-pyrazol-1-yl]-N-cyclopropyl-4-methylbenzamide.

Three. A pharmaceutical composition for the treatment of AECOPD in a human patient having <2% blood eosinophils, comprising administering to the patient three separate therapeutically effective doses of 3-[5-amino-4-(3-cyanobenzoyl)-pyrazol-1-yl]-N-cyclopropyl-4-methylbenzamide over a period of not longer than ten days with at least one day between every dose.

Four. A method for the treatment of AECOPD in a human patient having <2% blood eosinophils, comprising administering to the human patient three separate therapeutically effective doses of 3-[5-amino-4-(3-cyanobenzoyl)-pyrazol-1-yl]-N-cyclopropyl-4-methylbenzamide over a period of not longer than ten days with at least one day between every dose.

Five. The composition or method according to three or four, wherein the three doses are administered for a period of not longer than over 7 consecutive days with at least one day between every dose.

Six. The composition or method according to three or four, wherein the three separate doses are administered for a period of five days with at least one day between every dose.

Seven. The composition or method according to any of three to six, wherein the dosing is on days 1, 3 and 5.

Eight. The composition or method according to any of one to seven, wherein the therapeutically effective oral unit dose of 3-[5-amino-4-(3-cyanobenzoyl)-pyrazol-1-yl]-N-cyclopropyl-4-methylbenzamide, when given orally, is in the range of 10 mg-75 mg.

Nine. The composition or method according to any of three to eight, wherein the amount of the three separate therapeutically effective doses of 3-[5-amino-4-(3-cyanobenzoyl)-pyrazol-1-yl]-N-cyclopropyl-4-methylbenzamide is reduced over the course of the three separate administrations.

Ten. The composition or method according to any of three to nine, wherein the initial dose of 3-[5-amino-4-(3-cyanobenzoyl)-pyrazol-1-yl]-N-cyclopropyl-4-methylbenzamide is at least 20% greater than either of the subsequent doses, preferably at least 30% greater, more preferably 40% greater, most preferably 50% to 100% greater than the subsequent doses.

Eleven. The composition or method according to any of one to ten, wherein the blood eosinophils level is expressed as the percentage of white cells in peripheral blood of the human patient.

Twelve. The composition or method according to any of one to four, wherein the dosing is on days 1, 6 and 10.

Thirteen. Administrable doses, preferably unit doses, to be administered over a period of 10 days, and there must be at least one day between each dose administration. Preferably, the dose administration takes place on days 1, 6 and 10.

The various features and embodiments of the present invention, referred to in individual sections above apply, as appropriate, to other sections, mutatis mutandis.

Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for reducing the rate of reoccurrence of acute exacerbations of COPD in a human patient, comprising administering to a human patient in need thereof a first dosing regimen comprising three separate therapeutically effective doses of 3-[5-amino-4-(3-cyanobenzoyl)-pyrazol-1-yl]-N-cyclopropyl-4-methylbenzamide or a pharmaceutically acceptable derivates thereof over a period of not longer than seven days with at least one day between every dose, and a second dosing regimen comprising repeating the administration to the patient of the three doses of 3-[5-amino-4-(3-cyanobenzoyl)-pyrazol-1-yl]-N-cyclopropyl-4-methylbenzamide or a pharmaceutically acceptable derivative thereof after a 3-[5-amino-4-(3-cyanobenzoyl)-pyrazol-1-yl]-N-cyclopropyl-4-methylbenzamide treatment hiatus of at least 1 month from the start of the preceding administration.

2. A method for the preventing the development of an acute exacerbation of COPD in a human patient having COPD, comprising administering to a patient in need thereof an effective dose or doses of 3-[5-amino-4-(3-cyanobenzoyl)-pyrazol-1-yl]-N-cyclopropyl-4-methylbenzamide or a pharmaceutically acceptable derivates thereof over a period of not longer than seven days with at least one day between every dose, and repeating the administration to the patient of the effective dose or doses of 3-[5-amino-4-(3-cyanobenzoyl)-pyrazol-1-yl]-N-cyclopropyl-4-methylbenzamide or a pharmaceutically acceptable derivative thereof after a 3-[5-amino-4-(3-cyanobenzoyl)-pyrazol-1-yl]-N-cyclopropyl-4-methylbenzamide treatment hiatus of at least 1 month from the start of the preceding administration.

3. The method of claim 1, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is at least 2 months from the start of the preceding administration.

4. The method of claim 3, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is at least 3 months from the start of the preceding administration.

5. The method of claim 1, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is less than 7 months after the start of the preceding administration.

6. The method of claim 5, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is less than 6 months after the start of the preceding administration.

7. The method of claim 1, further comprising repeating the administration to the patient of the three doses of 3-[5-amino-4-(3-cyanobenzoyl)-pyrazol-1-yl]-N-cyclopropyl-4-methylbenzamide or a pharmaceutically acceptable derivative thereof after a further 3-[5-amino-4-(3-cyanobenzoyl)-pyrazol-1-yl]-N-cyclopropyl-4-methylbenzamide treatment hiatus of at least 1 month from the start of the preceding administration.

8. The method of claim 1, comprising administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, wherein the dosing is on days 1, 4 and 7.

9. The method of claim 1, comprising administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, over a period of five days with at least one day between every dose administration.

10. The method of claim 1, wherein three doses of 3-[5-amino-4-(3-cyanobenzoyl)-pyrazol-1-yl]-N-cyclopropyl-4-methylbenzamide are administered and wherein the amount of the three separate therapeutically effective doses of 3-[5-amino-4-(3-cyanobenzoyl)-pyrazol-1-yl]-N-cyclopropyl-4-methylbenzamide or a pharmaceutically acceptable derivative thereof is reduced over the course of the three separate administrations.

11. The method of claim 1, wherein three doses of 3-[5-amino-4-(3-cyanobenzoyl)-pyrazol-1-yl]-N-cyclopropyl-4-methylbenzamide are administered and wherein the initial dose of 3-[5-amino-4-(3-cyanobenzoyl)-pyrazol-1-yl]-N-cyclopropyl-4-methylbenzamide or a pharmaceutically acceptable derivative thereof is at least 20% greater than either of the subsequent doses.

12. The method of claim 11, wherein three doses of 3-[5-amino-4-(3-cyanobenzoyl)-pyrazol-1-yl]-N-cyclopropyl-4-methylbenzamide or a pharmaceutically acceptable derivative thereof are administered and wherein the initial dose of 3-[5-amino-4-(3-cyanobenzoyl)-pyrazol-1-yl]-N-cyclopropyl-4-methylbenzamide is at least 50% to 100% greater than the subsequent doses.

13. The method of claim 2, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is at least 2 months from the start of the preceding administration.

14. The method of claim 13, wherein the 3-[5-amino-4-(3-cyanobenzoyl)-pyrazol-1-yl]-N-cyclopropyl-4-methylbenzamide treatment hiatus prior to the repeat administration of 3-[5-amino-4-(3-cyanobenzoyl)-pyrazol-1-yl]-N-cyclopropyl-4-methylbenzamide or a pharmaceutically acceptable derivative thereof is less than 7 months after the start of the preceding administration.

15. The method of claim 2, further comprising repeating the administration to the patient of the three doses of 3-[5-amino-4-(3-cyanobenzoyl)-pyrazol-1-yl]-N-cyclopropyl-4-methylbenzamide or a pharmaceutically acceptable derivative thereof after a further 3-[5-amino-4-(3-cyanobenzoyl)-pyrazol-1-yl]-N-cyclopropyl-4-methylbenzamide treatment hiatus of at least 1 month from the start of the preceding administration.

16. The method of claim 2, comprising administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, wherein the dosing is on days 1, 4 and 7.

17. The method of claim 2, comprising administering three separate doses of a pharmaceutical composition comprising 3-[5-amino-4-(3-cyanobenzoyl)-pyrazol-1-yl]-N-cyclopropyl-4-methylbenzamide or a pharmaceutically acceptable derivative thereof, over a period of five days with at least one day between every dose administration.

18. The method of claim 2, wherein three doses of 3-[5-amino-4-(3-cyanobenzoyl)-pyrazol-1-yl]-N-cyclopropyl-4-methylbenzamide or a pharmaceutically acceptable derivative thereof are administered and wherein the amount of the three separate therapeutically effective doses of 3-[5-amino-4-(3-cyanobenzoyl)-pyrazol-1-yl]-N-cyclopropyl-4-methylbenzamide or a pharmaceutically acceptable derivative thereof is reduced over the course of the three separate administrations.

19. A kit comprising at least six separate therapeutically effective doses of 3-[5-amino-4-(3-cyanobenzoyl)-pyrazol-1-yl]-N-cyclopropyl-4-methylbenzamide or a pharmaceutically acceptable derivative thereof, and instructions for treating a human patient suffering from an acute exacerbation of COPD, said instructions comprising directions for administering the first, second and third doses separately over a period of not longer than seven days with a least one day between every dose administration, and directions for administering the fourth, fifth, and sixth doses separately over a period of not longer than seven days with a least one day between every dose administration, said fourth dose being administered at least 1 month after the administration of the first dose.

20. The method of claim 1 wherein said patient is not experiencing an acute exacerbation of COPD at the start of said second dosing regimen.

* * * * *